US009705095B2

(12) United States Patent
Youfu et al.

(10) Patent No.: US 9,705,095 B2
(45) Date of Patent: Jul. 11, 2017

(54) ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, COATING SOLUTION FOR NON-LIGHT-EMITTING ORGANIC SEMICONDUCTOR DEVICE, AND ORGANIC SEMICONDUCTOR FILM FOR NON-LIGHT-EMITTING ORGANIC SEMICONDUCTOR DEVICE

(71) Applicant: FUJIFILM Corporation, Tokyo (JP)

(72) Inventors: Katsuyuki Youfu, Kanagawa (JP); Yuki Hirai, Kanagawa (JP); Kensuke Masui, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/199,138

(22) Filed: Jun. 30, 2016

(65) Prior Publication Data

US 2016/0315271 A1    Oct. 27, 2016

Related U.S. Application Data

(63) Continuation of application No. PCT/JP2015/050003, filed on Jan. 5, 2015.

(30) Foreign Application Priority Data

Jan. 9, 2014    (JP) ................................ 2014-002608

(51) Int. Cl.
*H01L 51/00* (2006.01)
*C07C 25/24* (2006.01)
(Continued)

(52) U.S. Cl.
CPC ........ *H01L 51/0074* (2013.01); *C07C 17/263* (2013.01); *C07C 25/24* (2013.01);
(Continued)

(58) Field of Classification Search
CPC ............. H01L 51/0071; H01L 51/0072; H01L 51/0073; H01L 51/0074
See application file for complete search history.

(56) References Cited

U.S. PATENT DOCUMENTS 8,203,141 B2   6/2012 Kim et al.
2008/0045511 A1   2/2008 Kennedy-Smith et al.
(Continued)

FOREIGN PATENT DOCUMENTS

JP   2011-046687 A   3/2011
JP   2013-220996 A   10/2013
(Continued)

OTHER PUBLICATIONS

International Search Report issued in PCT/JP2015/050003; mailed Feb. 10, 2015.
(Continued)

*Primary Examiner* — Seahvosh Nikmanesh
(74) *Attorney, Agent, or Firm* — Studebaker & Brackett PC

(57) ABSTRACT

Provided are an organic transistor having high carrier mobility that contains a compound represented by the following formula in a semiconductor active layer; a compound; an organic semiconductor material for a non-light-emitting organic semiconductor device; a material for an organic transistor; a coating solution for a non-light-emitting organic semiconductor device; and an organic semiconductor film for a non-light-emitting organic semiconductor device (each of $X^1$ and $X^2$ represents $NR^{13}$, an O atom, or a S atom; $A^1$
(Continued)

represents CR⁷ or a N atom; A² represents CR⁸ or a N atom; R¹³ represents a hydrogen atom, an alkyl group, an alkenyl group, an alkynyl group, or an acyl group; each of R¹ to R⁸ independently represents a hydrogen atom or a substituent; at least one of $R^1$, $R^2$, $R^3$, $R^4$, $R^5$, $R^6$, $R^7$, or $R^8$ is a substituent represented by -L-R; L represents a divalent linking group having a specific structure; and R represents an alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a trialkylsilyl group).

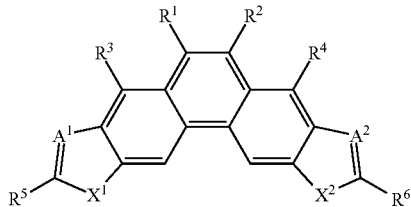

24 Claims, 1 Drawing Sheet

(51) Int. Cl.

| | | |
|---|---|---|
| C07C 39/373 | (2006.01) | |
| C07D 487/04 | (2006.01) | |
| C07D 493/04 | (2006.01) | |
| C07D 498/04 | (2006.01) | |
| C07C 47/55 | (2006.01) | |
| C07D 495/04 | (2006.01) | |
| C07D 513/04 | (2006.01) | |
| C07F 7/08 | (2006.01) | |
| C07C 17/263 | (2006.01) | |
| H01L 51/05 | (2006.01) | |

(52) U.S. Cl.
CPC ............ *C07C 39/373* (2013.01); *C07C 47/55* (2013.01); *C07D 487/04* (2013.01); *C07D 493/04* (2013.01); *C07D 495/04* (2013.01); *C07D 498/04* (2013.01); *C07D 513/04* (2013.01); *C07F 7/0818* (2013.01); *H01L 51/0068* (2013.01); *H01L 51/0072* (2013.01); *H01L 51/0073* (2013.01); *C07C 2103/26* (2013.01); *H01L 51/0545* (2013.01); *H01L 51/0558* (2013.01); *H01L 51/0566* (2013.01)

(56) References Cited

U.S. PATENT DOCUMENTS

| | | | |
|---|---|---|---|
| 2010/0283043 A1* | 11/2010 | Nishimura | C09K 11/06 257/40 |
| 2011/0049485 A1 | 3/2011 | Kim et al. | |
| 2014/0061616 A1 | 3/2014 | Sunagawa et al. | |
| 2014/0077191 A1* | 3/2014 | Mizutani | C07D 471/04 257/40 |

FOREIGN PATENT DOCUMENTS

| | | |
|---|---|---|
| KR | 10-2012-0081539 A | 7/2012 |
| WO | 2007/128601 A2 | 11/2007 |
| WO | 2012/090462 A1 | 7/2012 |

OTHER PUBLICATIONS

International Preliminary Report on Patentability issued in PCT/JP2015/050003; mailed Aug. 11, 2015.
Molnár et al.; Ring Transformation of Unsaturated N-Bridgehead Fused Pyrimidin-4(3H)-ones: Role of Repulsive Electrostatic Nonbonded Interaction; The Journal of Organic Chemistry; 2011; pp. 696-699.
Zhu et al.; Conjugated Polymers Containing 2,3-Dialkoxybenzene and Iptycene Building Blocks; Organic Letters; 2001; pp. 3471-3474.
Rieger et al.; Tetrathiahexacene as Building Block for Solution-Processable Semiconducting Polymers: Exploring the Monomer Size Limit; Macromolecules; 2010; pp. 6264-6267.
Ruzié et al.; Synthesis of 1,6-, 2,7-, 3,8-, and 4,9-Isomers of Didodecyl[1]benzothieno[3,2-b][1]benzothiophenes; The Journal of Organic Chemistry; 2013; pp. 7741-7748.
Huang et al.; Enhanced Performance of Benzothieno[3,2-b]thiophene (BTT)-Based Bottom-Contact Thin-Film Transistors; Chemistry A European Journal; 2013; pp. 3721-3728.
Powell et al.; Iodide Acceleration in the Pd-Catalyzed Coupling of Aromatic 1,2-Ditriflates with Alkynes: Synthesis of Enediynes; Tetrahedron Letters; 1996; pp. 7901-7904.
Some et al.; Synthesis of substituted benzene derivatives by homo- and hetero-coupling of 2-bromobenzaldehyde and bromovinylaldehydes followed by McMurry coupling; Tetrahedron Letters; 2006; pp. 1221-1224.
Shinamura et al.; Linear- and Angular-Shaped Naphthodithiophenes: Selective Synthesis, Properties, and Application to Organic Field-Effect Transistors; Journal of the American Chemical Society; 2011; pp. 5024-5035.
Coropceanu et al.; Vibronic Coupling in Organic Semiconductors: The Case of Fused Polycyclic Benzene-Thiophene Structures; Chemistry A European Journal; 2006; pp. 2073-2080.
Liu et al.; Palladium-Catalyzed Cocyclotrimerization of Allenes with Arynes: Selective Synthesis of Phenanthrenes; The Journal of Organic Chemistry; 2009; pp. 3199-3202.
Notification of Transmittal of Translation of the International Preliminary Report on Patentability; PCT/JP2015/050003 issued on Jul. 14, 2016.
An Office Action; "Notification of Reasons for Refusal," issued by the Japanese Patent Office on Jan. 31, 2017, which corresponds to Japanese Patent Application No. 2014-002608 and is related to U.S. Appl. No. 15/199,138; with English language translation.

\* cited by examiner

ORGANIC TRANSISTOR, COMPOUND, ORGANIC SEMICONDUCTOR MATERIAL FOR NON-LIGHT-EMITTING ORGANIC SEMICONDUCTOR DEVICE, MATERIAL FOR ORGANIC TRANSISTOR, COATING SOLUTION FOR NON-LIGHT-EMITTING ORGANIC SEMICONDUCTOR DEVICE, AND ORGANIC SEMICONDUCTOR FILM FOR NON-LIGHT-EMITTING ORGANIC SEMICONDUCTOR DEVICE

CROSS-REFERENCE TO RELATED APPLICATIONS

This application is a Continuation of PCT International Application No. PCT/JP2015/050003, filed on Jan. 5, 2015, which claims priority under 35 U.S.C. Section 119(a) to Japanese Patent Application No. 2014-002608 filed on Jan. 9, 2014. Each of the above applications is hereby expressly incorporated by reference, in its entirety, into the present application.

BACKGROUND OF THE INVENTION

1. Field of the Invention

The present invention relates to an organic transistor, an organic semiconductor film, an organic semiconductor material, and the like. Specifically, the present invention relates to a compound having a phenanthrene skeletal structure condensed with two 5-membered heterocyclic rings, an organic transistor, an organic semiconductor material for a non-light-emitting organic semiconductor device, a material for an organic transistor, a coating solution for a non-light-emitting organic semiconductor device, an organic semiconductor film for a non-light-emitting organic semiconductor device, and a compound which is an intermediate for synthesizing the aforementioned compound.

2. Description of the Related Art

The devices using organic semiconductor materials are drawing great attention because they are expected to be superior in various aspects to the devices using inorganic semiconductor materials of the related art such as silicon. Examples of the devices using organic semiconductor materials include a photoelectric conversion element such as an organic solar cell or a solid-state imaging element using organic semiconductor materials as photoelectric conversion materials, an organic transistor (referred to as an organic thin-film transistor in some cases) having non-light-emitting properties (in the present specification, "non-light-emitting" refers to properties by which a luminous efficiency of equal to or less than 1 lm/W is obtained in a case where electric currents are applied to a device at a current density of 0.1 mW/cm$^2$ at room temperature in the atmosphere; non-light-emitting organic semiconductor devices mean organic semiconductor devices excluding light-emitting organic semiconductor devices such as organic electroluminescence elements), and the like. The devices using organic semiconductor materials are likely to make it possible to prepare large area elements at lower temperature and lower costs compared to the devices using inorganic semiconductor materials. Furthermore, the characteristics of the materials can be easily changed by varying the molecular structure thereof. Therefore, the materials show a wide variation and can realize functions or elements that cannot be obtained by inorganic semiconductor materials.

Regarding materials for organic transistors, the use of a compound having a condensed ring in a semiconductor active layer is investigated for improving carrier mobility.

As the compound having a condensed ring, KR-10-2012-0081539A describes a phenanthropyrrole compound having a bulky substituent on a N atom.

SUMMARY OF THE INVENTION

Under the circumstances described above, the inventors of the present invention investigated an organic transistor using the compound described in KR-10-2012-0081539A. As a result, they found that even if the compound described in KR-10-2012-0081539A, which does not describe an example of using the compound in an organic transistor, is used in a semiconductor active layer of an organic transistor, the carrier mobility is low, and high transistor characteristics cannot be obtained.

Therefore, in order to solve the above problems of the related art, the inventors of the present invention continued investigation. An object of the present invention is to provide an organic transistor having high carrier mobility.

As a result of conducting intensive investigation for achieving the above objects, the inventors of the present invention obtained knowledge that by condensing two 5-membered heterocyclic rings in specific combination in specific positions, high carrier mobility can be obtained when the resulting compound is used in a semiconductor active layer of a organic transistor. Based on the knowledge, the inventors accomplished the present invention.

The present invention as specific means for achieving the above object is constituted as below.

[1] An organic transistor comprising a compound represented by the following Formula (1) in a semiconductor active layer:

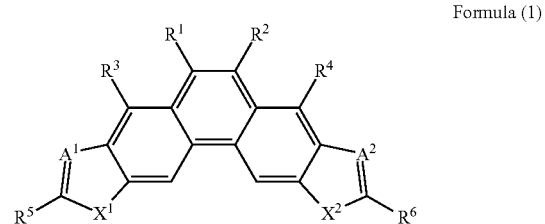

Formula (1)

in Formula (1), each of $X^1$ and $X^2$ independently represents $NR^{13}$, an O atom, or a S atom, $A^1$ represents $CR^7$ or a N atom, $A^2$ represents $CR^8$ or a N atom, $R^{13}$ represents a hydrogen atom, an alkyl group, an alkenyl group, an alkynyl group, an acyl group, an aryl group, or a heteroaryl group, each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, and R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted tri-alkylsilyl group;
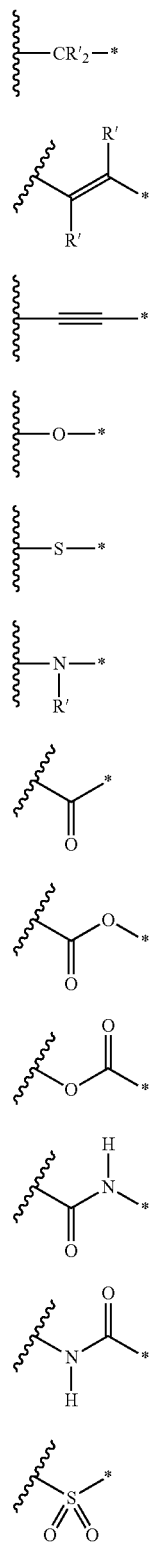
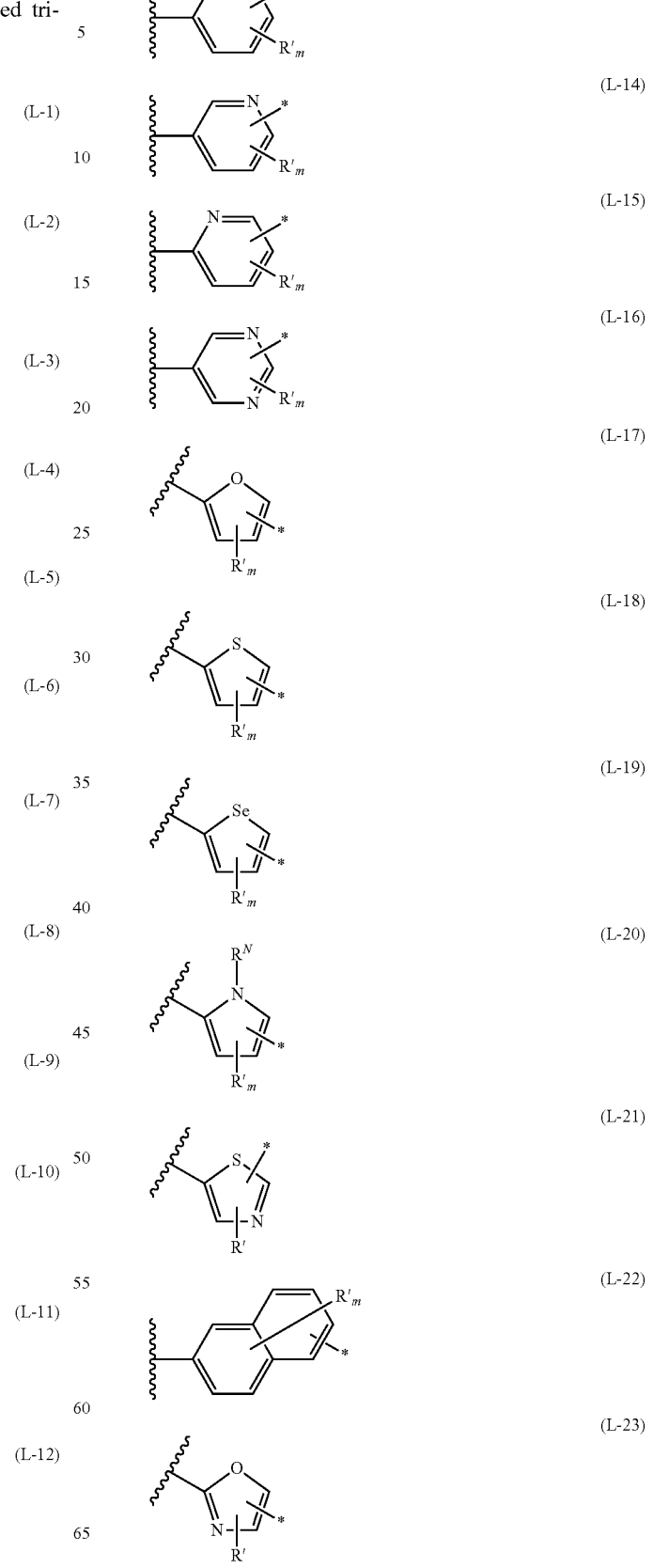

-continued

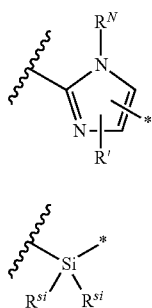
(L-24)

(L-25)

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

[2] The organic transistor described in [1], in which the compound represented by Formula (1) is preferably a compound represented by the following Formula (2-1) or (2-2):

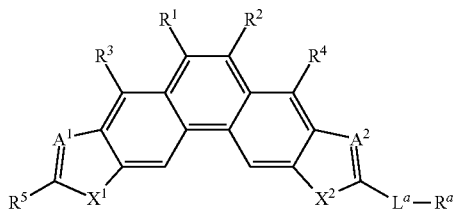
Formula (2-1)

in Formula (2-1), each of $X^1$ and $X^2$ independently represents an O atom or a S atom, $A^1$ represents $CR^7$ or a N atom, $A^2$ represents $CR^8$ or a N atom, each of $R^1$ to $R^5$, $R^7$, and $R^8$ independently represents a hydrogen atom or a substituent, $R^5$ is not a group represented by $-L^a-R^a$, $L^a$ represents a divalent linking group represented by any of the following Formulae (L-1) to (L-25) or a divalent linking group in which two or more divalent linking groups represented by any of the following Formulae (L-1) to (L-25) are bonded to each other, and $R^a$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, an oligosiloxane group having two or more silicon atoms, a siloxane group, or a substituted or unsubstituted trialkylsilyl group;

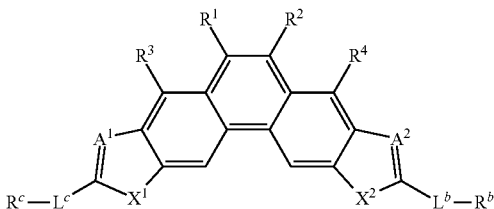
Formula (2-2)

in Formula (2-2), each of $X^1$ and $X^2$ independently represents an O atom or a S atom, $A^1$ represents $CR^7$ or a N atom, $A^2$ represents $CR^8$ or a N atom, each of $R^1$ to $R^4$, $R^7$, and $R^8$ independently represents a hydrogen atom or a substituent, each of $L^b$ and $L^c$ independently represents a divalent linking group represented by any of the following Formulae (L-1) to (L-25) or a divalent linking group in which two or more divalent linking groups represented by any of the following Formulae (L-1) to (L-25) are bonded to each other, and each of $R^b$ and $R^c$ independently represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

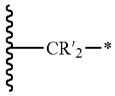
(L-1)

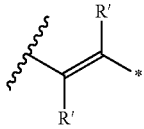
(L-2)

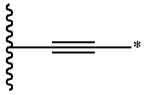
(L-3)

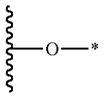
(L-4)

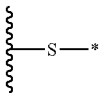
(L-5)

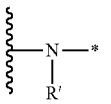
(L-6)

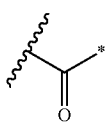
(L-7)

-continued

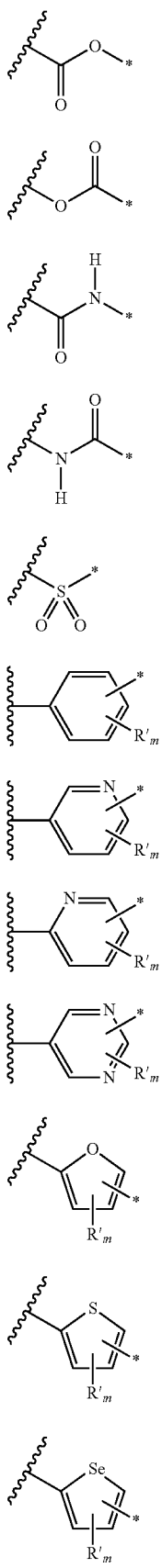

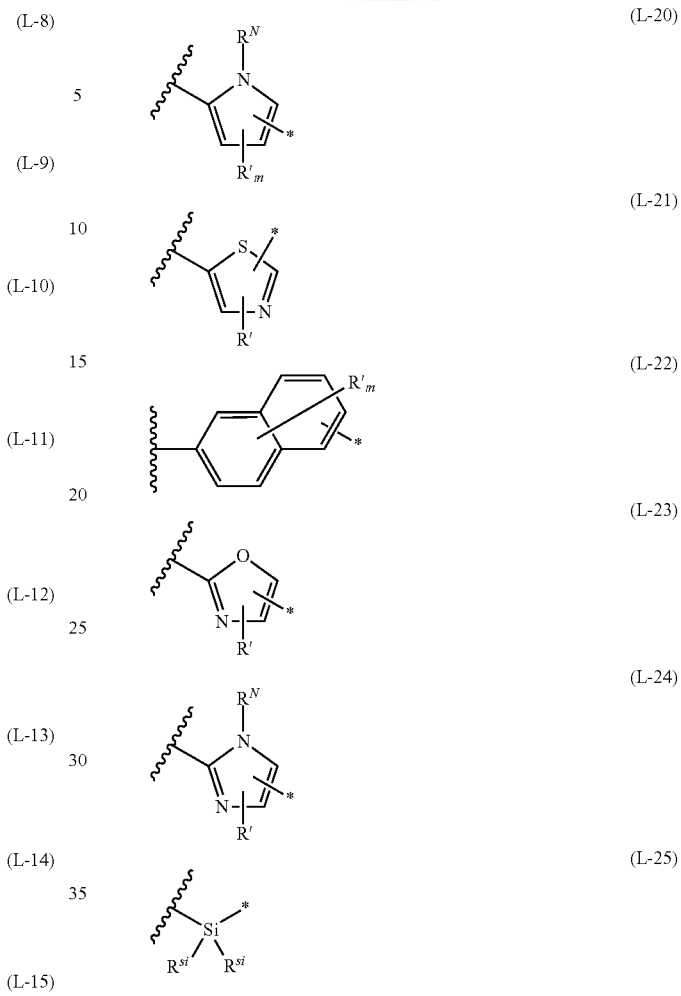

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

[3] The organic transistor described in [1] or [2], in which in Formula (1), (2-1), or (2-2), $A^1$ is preferably $CR^7$ or $A^2$ is preferably $CR^8$, and each of $R^7$ and $R^8$ preferably independently represents a hydrogen atom or a substituent.

[4] The organic transistor described in any one of [1] to [3], in which in Formula (1), (2-1), or (2-2), at least one of $X^1$ or $X^2$ is preferably a S atom.

[5] The organic transistor described in any one of [1] to [4], in which in Formula (1), (2-1), or (2-2), each of L, $L^a$, $L^b$, and $L^c$ is preferably a divalent linking group represented by any of Formulae (L-1) to (L-5), (L-13), (L-17), and (L-18) or a divalent linking group in which two or more divalent linking groups represented by any of the above formulae are bonded to each other.

[6] The organic transistor described in any one of [1] to [5], in which in Formula (1), (2-1), or (2-2), each of L, $L^a$, $L^b$, and $L^c$ is preferably a divalent linking group represented by any of Formulae (L-1), (L-3), (L-13), and (L-18) or a divalent linking group in which a divalent linking group represented by any one of Formulae (L-3), (L-13), and (L-18) is bonded to a divalent linking group represented by Formula (L-1).

[7] The organic transistor described in any one of [1] to [6], in which in Formula (1), (2-1), or (2-2), each of R, $R^a$, $R^b$, and $R^c$ is preferably a substituted or unsubstituted alkyl group.

[8] A compound represented by the following Formula (1):

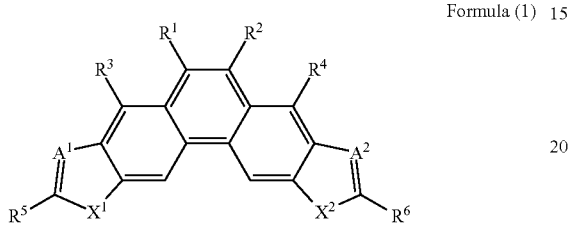

Formula (1)

in Formula (1), each of $X^1$ and $X^2$ independently represents $NR^{13}$, an O atom, or a S atom, $A^1$ represents $CR^7$ or a N atom, $A^2$ represents $CR^8$ or a N atom, $R^{13}$ represents a hydrogen atom, an alkyl group, an alkenyl group, an alkynyl group, an acyl group, an aryl group, or a heteroaryl group, each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

-L-R　　　　　Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, and R represents a substituted or unsubstituted alkyl group, a cyano group, a vinyl group, an ethynyl group, an oxyethylene group, an oligo-oxyethylene group in which a repetition number of an oxyethylene unit is equal to or greater than 2, a siloxane group, an oligosiloxane group having two or more silicon atoms, or a substituted or unsubstituted trialkylsilyl group;

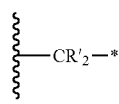

(L-1)

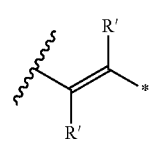

(L-2)

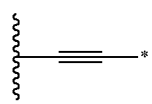

(L-3)

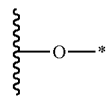

(L-4)

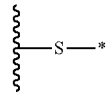

(L-5)

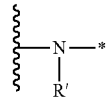

(L-6)

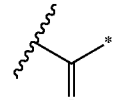

(L-7)

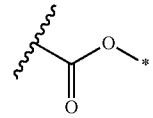

(L-8)

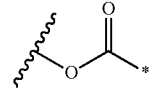

(L-9)

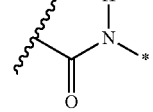

(L-10)

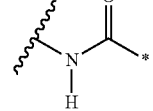

(L-11)

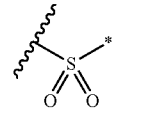

(L-12)

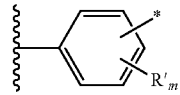

(L-13)

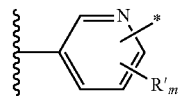

(L-14)

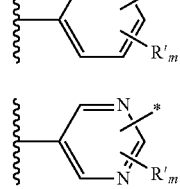

(L-15)

(L-16)

-continued (L-17)
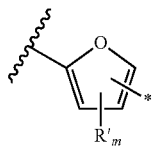

(L-18)
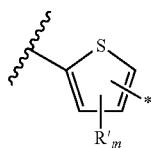

(L-19)
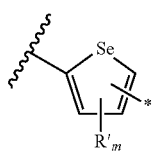

(L-20)
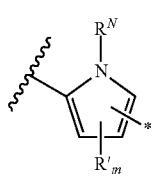

(L-21)
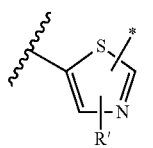

(L-22)
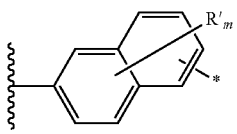

(L-23)
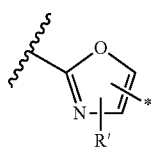

(L-24)
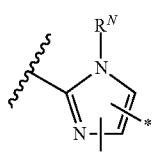

(L-25)
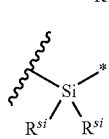

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

[9] The compound described in [8], in which the compound represented by Formula (1) is preferably a compound represented by the following Formula (2-1) or (2-2):

Formula (2-1)

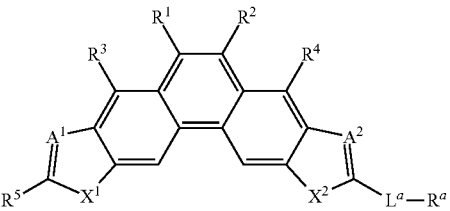

in Formula (2-1), each of $X^1$ and $X^2$ independently represents an O atom or a S atom, $A^1$ represents $CR^7$ or a N atom, $A^2$ represents $CR^8$ or a N atom, each of $R^1$ to $R^5$, $R^7$, and $R^8$ independently represents a hydrogen atom or a substituent, $R^5$ is not a group represented by -$L^a$-$R^a$, $L^a$ represents a divalent linking group represented by any of the following Formulae (L-1) to (L-25) or a divalent linking group in which two or more divalent linking groups represented by any of the following Formulae (L-1) to (L-25) are bonded to each other, and $R^a$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, an oligosiloxane group having two or more silicon atoms, a siloxane group, or a substituted or unsubstituted trialkylsilyl group;

Formula (2-2)

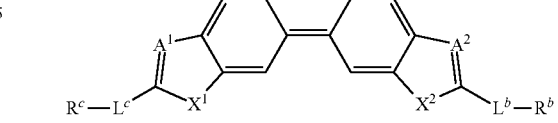

in Formula (2-2), each of $X^1$ and $X^2$ independently represents an O atom or a S atom, $A^1$ represents $CR^7$ or a N atom, $A^2$ represents $CR^8$ or a N atom, each of $R^1$ to $R^4$, $R^7$, and $R^8$ independently represents a hydrogen atom or a substituent, each of $L^b$ and $L^c$ independently represents a divalent linking group represented by any of the following Formulae (L-1) to (L-25) or a divalent linking group in which two or more divalent linking groups represented by any of the following Formulae (L-1) to (L-25) are bonded to each other, and each of $R^b$ and $R^c$ independently represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;
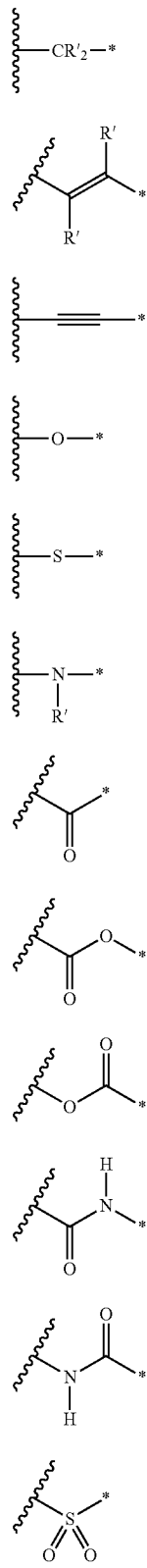
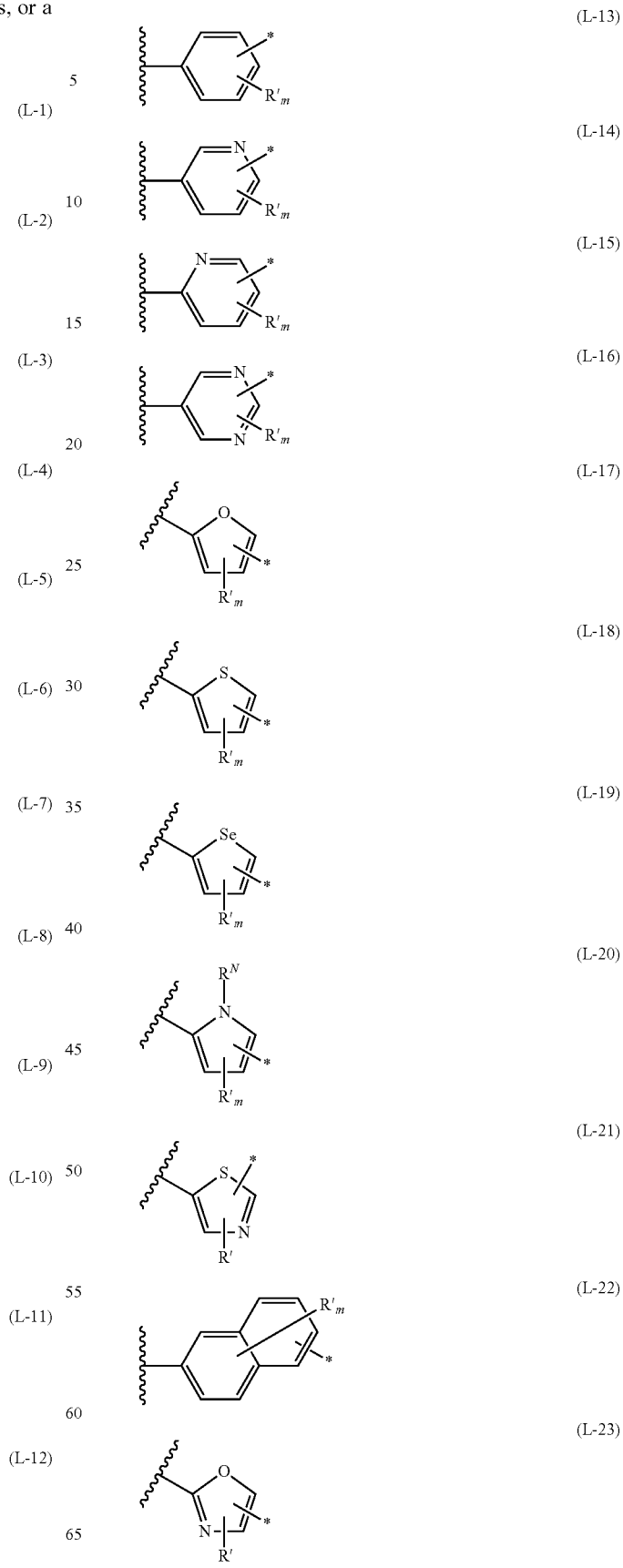

-continued

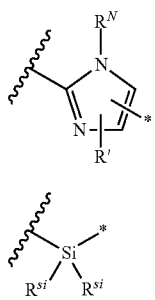
(L-24)

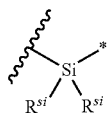
(L-25)

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

[10] The compound described in [8] or [9], in which in Formula (1), (2-1), or (2-2), $A^1$ is preferably $CR^7$ or $A^2$ is preferably $CR^8$, and each of $R^7$ and $R^8$ preferably independently represents a hydrogen atom or a substituent.

[11] The compound described in any one of [8] to [10], in which in Formula (1), (2-1), or (2-2), at least one of $X^1$ or $X^2$ is preferably a S atom.

[12] The compound described in any one of [8] to [11], in which in Formula (1), (2-1), or (2-2), each of L, $L^a$, $L^b$, and $L^c$ is preferably a divalent linking group represented by any of Formulae (L-1) to (L-5), (L-13), (L-17), and (L-18) or a divalent linking group in which two or more divalent linking groups represented by any of the above formulae are bonded to each other.

[13] The compound represented by any one of [8] to [12], in which in Formula (1), (2-1), or (2-2), each of L, $L^a$, $L^b$, and $L^c$ is preferably a divalent linking group represented by any of Formulae (L-1), (L-3), (L-13), and (L-18) or a divalent linking group in which a divalent linking group represented by any one of Formulae (L-3), (L-13), and (L-18) is bonded to a divalent linking group represented by Formula (L-1).

[14] The compound represented by any one of [8] to [13], in which in Formula (1), (2-1), or (2-2), each of R, $R^a$, $R^b$, and $R^c$ is preferably a substituted or unsubstituted alkyl group.

[15] An organic semiconductor material for a non-light-emitting organic semiconductor device, comprising the compound described in any one of [8] to [14].

[16] A material for an organic transistor, comprising the compound described in any one of [8] to [14].

[17] A coating solution for a non-light-emitting organic semiconductor device, comprising the compound described in any one of [8] to [14].

[18] A coating solution for a non-light-emitting organic semiconductor device, comprising the compound described in any one of [8] to [14] and a polymer binder.

[19] An organic semiconductor film for a non-light-emitting organic semiconductor device, comprising the compound described in any one of [8] to [14].

[20] An organic semiconductor film for a non-light-emitting organic semiconductor device, comprising the compound described in any one of [8] to [14] and a polymer binder.

[21] The organic semiconductor film for a non-light-emitting organic semiconductor device described in [19] or [20] that is preferably prepared by a solution coating method.

[22] A compound represented by the following Formula (3):

Formula (3)

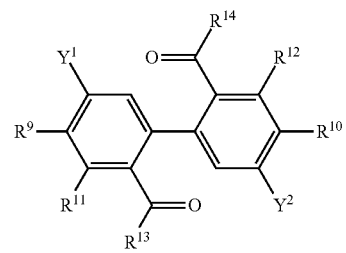

in Formula (3), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, and each of $R^{11}$ to $R^{14}$ independently represents a hydrogen atom or a substituent.

[23] A compound represented by the following Formula (4):

Formula (4)

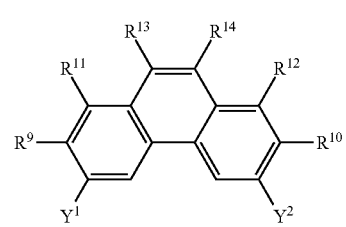

in Formula (4), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, and each of $R^{11}$ to $R^{14}$ independently represents a hydrogen atom or a substituent.

[24] The compound described in [22] or [23] that is preferably an intermediate compound of the compound described in any one of [8] to [14].

According to the present invention, it is possible to provide an organic transistor having high carrier mobility.

DESCRIPTION OF THE PREFERRED EMBODIMENTS

Figure 1:
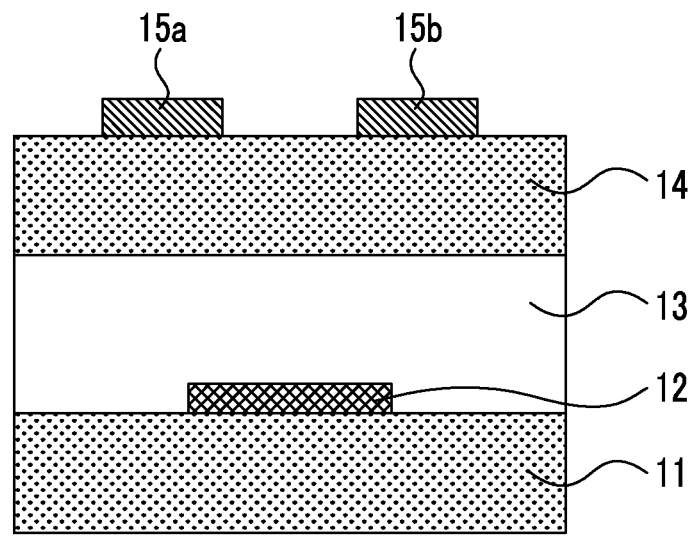
FIG. 1 is a schematic view showing a section of an exemplary structure of an organic transistor of the present invention.

Hereinafter, the present invention will be specifically described. The constituents described below will be explained based on representative embodiments or specific examples, but the present invention is not limited to the embodiments. In the present specification, a range of numerical values described using "to" means a range including the numerical values listed before and after "to" as a lower limit and an upper limit respectively.

In the present invention, unless otherwise specified, a hydrogen atom used in the description of each formula represents a hydrogen atom including an isotope (deuterium atom or the like). Furthermore, an atom constituting a substituent represents an atom including an isotope thereof.

[Organic Transistor]

An organic transistor of the present invention contains a compound represented by the following Formula (1) in a semiconductor active layer.

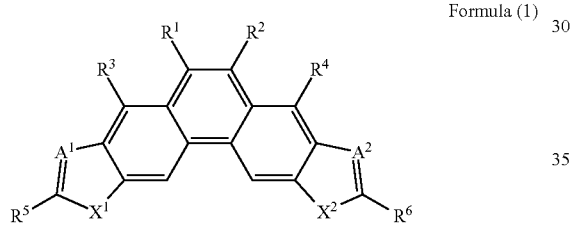

Formula (1)

In Formula (1), each of $X^1$ and $X^2$ independently represents $NR^{13}$, an O atom, or a S atom, $A^1$ represents $CR^7$ or a N atom, $A^2$ represents $CR^8$ or a N atom, $R^{13}$ represents a hydrogen atom, an alkyl group, an alkenyl group, an alkynyl group an acyl group, an aryl group, or a heteroaryl group, each of $R^1$ to $R^8$ independently represents a hydrogen atom or a substituent, at least one of $R^1$, $R^2$, $R^3$, $R^4$, $R^5$, $R^6$, $R^7$, or $R^8$ is a substituent represented by the following Formula (W):

-L-R  Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, and R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

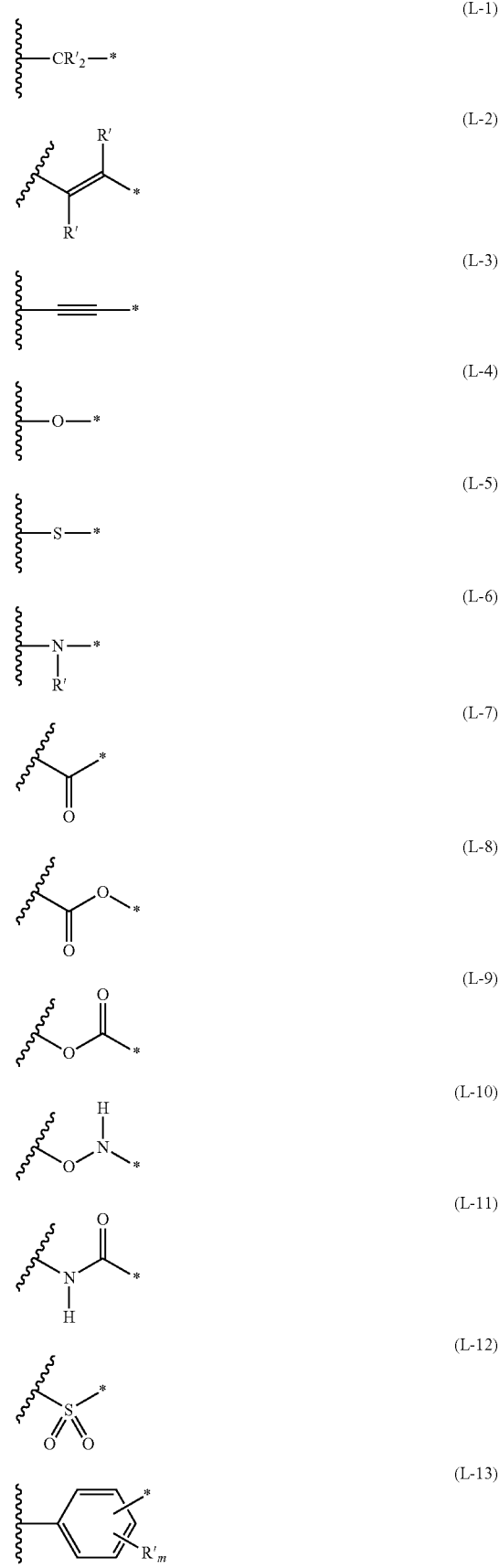

-continued (L-14) 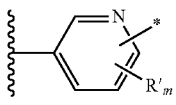

(L-15) 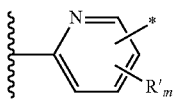

(L-16) 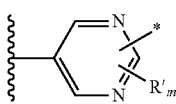

(L-17) 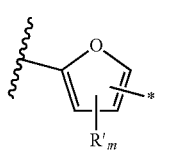

(L-18) 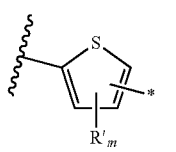

(L-19) 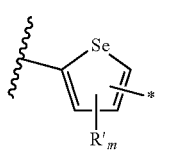

(L-20) 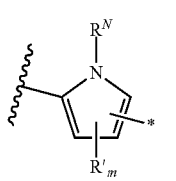

(L-21) 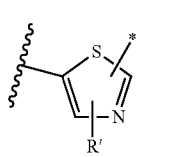

(L-22) 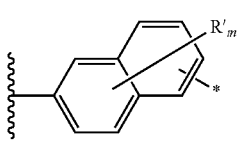

(L-23) 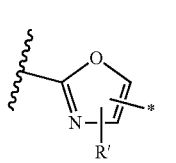

(L-24) 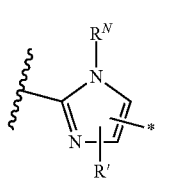

(L-25) 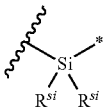

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

By containing the compound represented by Formula (1) in the semiconductor active layer, the organic transistor of the present invention has high carrier mobility.

Herein, KR-10-2012-0081539A describes a phenanthrodipyrrole compound whose skeleton seems to be similar to that of the compound of the present invention. However, the number of condensed rings of the compound described in KR-10-2012-0081539A is different from that of the compound of the present invention, the compound described in the above document has a bulky substituent on a N atom. Therefore, when the compound is crystallized, overlapping of HOMO does not sufficiently occur between molecules, and hence high carrier mobility is not obtained.

In contrast, the compound of the present invention is condensed with two 5-membered heterocyclic rings in specific combination in specific positions, and as a result, overlapping of HOMO sufficiently occurs in a phenanthrene skeleton, and the compound exhibits carrier mobility high enough for being used as a semiconductor material for a transistor.

It is preferable that the organic transistor of the present invention using the compound represented by Formula (1) shows only a slight threshold voltage shift after repeated driving. In order to reduce the threshold voltage shift after repeated driving, HOMO of the organic semiconductor material needs not to be too shallow or too deep. Furthermore, the chemical stability (particularly, resistance against air oxidation and stability against oxidation and reduction) of the organic semiconductor material, the heat stability of the film state, the high film density which makes it difficult for air or moisture to permeate the film, the film quality by which the film has small defectiveness such that charge accumulation does not easily occur, and the like are required. In addition, the higher the solubility of the compound represented by the Formula (1) in an organic solvent at the time of film formation, the further the threshold voltage shift after repeated driving can be reduced when the compound is used in the semiconductor active layer of the organic transistor. It is considered that because the compound represented by the Formula (1) satisfies the aforementioned requirements, the organic transistor shows only a slight threshold voltage shift after repeated driving. That is, in the organic transistor showing only a slight threshold voltage shift after repeated driving, the semiconductor active layer has high chemical stability, high film density, and the like, and thus the organic transistor can effectively function as a transistor over a long period of time.

Being useful as an organic EL element material does not mean being useful as a semiconductor material for an organic transistor, because the characteristics required for the organic compound vary between the organic EL element and the organic transistor. In the organic EL element, charges need to be transported in the film thickness direction (generally, several nanometers to hundreds of nanometers) of a general film. In contrast, in the organic transistor, charges (carriers) need to be transported a long distance between electrodes (generally, several micrometers to hundreds of micrometers) in the film plane direction, and hence extremely high carrier mobility is required. Accordingly, as the semiconductor material for an organic transistor, an organic compound showing highly ordered molecular arrangement and having high crystallinity is required. Furthermore, for the expression of high carrier mobility, the π-conjugate plane thereof is preferably upright against a substrate. On the other hand, for the organic EL element, in order to improve the luminous efficiency, an element having high luminous efficiency and uniformly emitting light in plane is required. Generally, an organic compound having high crystallinity causes luminescence defectiveness such as nonuniform in-plane electric field intensity, nonuniform luminescence, and quenching of luminescence. Therefore, as the material for an organic EL element, those having low crystallinity but having high amorphousness are desirable. Consequently, the use of the organic compound constituting the organic EL element material as an organic semiconductor material does not ensure that excellent transistor characteristics can be obtained.

Hereinafter, preferred aspects of the compound, the organic transistor of the present invention, and the like will be described.

<Compound Represented by Formula (1)>

The compound of the present invention is represented by Formula (1). In the organic transistor of the present invention, the compound of the present invention is contained in the semiconductor active layer which will be described later. That is, the compound of the present invention can be used as a material for the organic transistor.

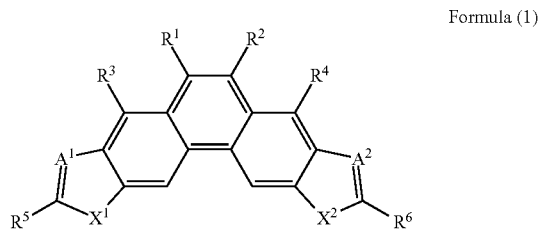

Formula (1)

In Formula (1), each of $X^1$ and $X^2$ independently represents $NR^{13}$, an O atom, or a S atom. From the viewpoint of the ease of synthesis, it is preferable that each of $X^1$ and $X^2$ is independently an O atom or a S atom. In contrast, from the viewpoint of improving the are preferably the same linking group. It is more preferable that both of X1 and X2 are a S atom.

$R^{13}$ represents a hydrogen atom, an alkyl group, an alkenyl group, an alkynyl group, an acyl group, an aryl group, or a heteroaryl group. $R^{13}$ is preferably a hydrogen atom, an alkyl group, an alkenyl group, an alkynyl group, or an acyl group, more preferably a hydrogen atom or an alkyl group, particularly preferably an alkyl group having 1 to 14 carbon atoms, and more particularly preferably an alkyl group having 1 to 4 carbon atoms.

In a case where $R^{13}$ represents an alkyl group, the alkyl group may be a linear, branched, or cyclic alkyl group. However, $R^{13}$ is preferably a linear alkyl group because then the linearity of the molecule can be improved, and hence the carrier mobility can be improved.

In Formula (1), $A^1$ represents $CR^7$ or a N atom, $A^2$ represents $CR^8$ or a N atom, and each of $R^7$ and $R^8$ independently represents a hydrogen atom or a substituent. It is preferable that $A^1$ is $CR^7$ or $A^2$ is $CR^8$. More preferably, $A^1$ is $CR^7$, and $A^2$ is $CR^8$. $A^1$ and $A^2$ may be the same as or different from each other, but it is preferable that they are the same as each other.

In Formula (1), $R^5$ and $R^7$ may or may not form a ring by being bonded to each other, but it is preferable that they do not form a ring by being bonded to each other.

In Formula (1), $R^5$ and $R^{13}$ may or may not form a ring by being bonded to each other, but it is preferable that they do not form a ring by being bonded to each other.

In Formula (1), $R^6$ and $R^8$ may or may not form a ring by being bonded to each other, but it is preferable that they do not form a ring by being bonded to each other.

In Formula (1), $R^6$ and $R^{13}$ may or may not form a ring by being bonded to each other, but it is preferable that they do not form a ring by being bonded to each other.

In Formula (1), each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

-L-R        Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group:

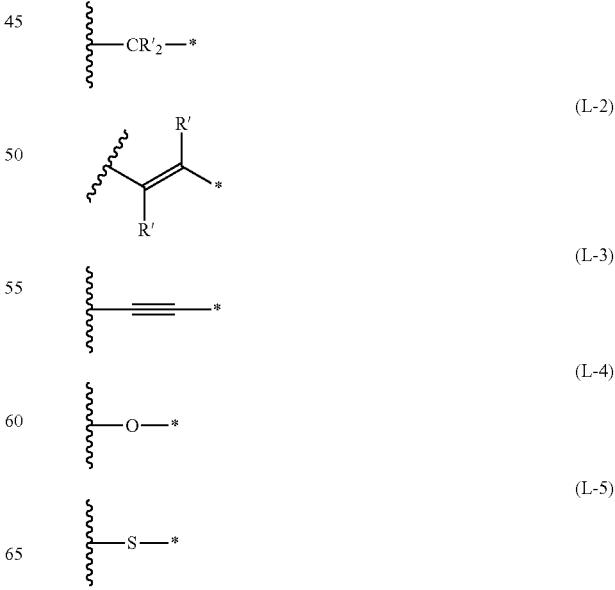

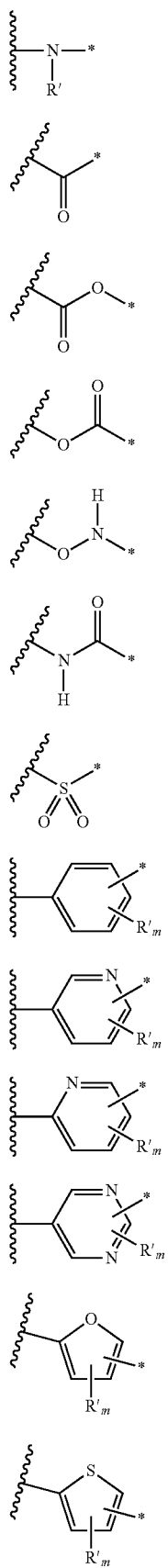
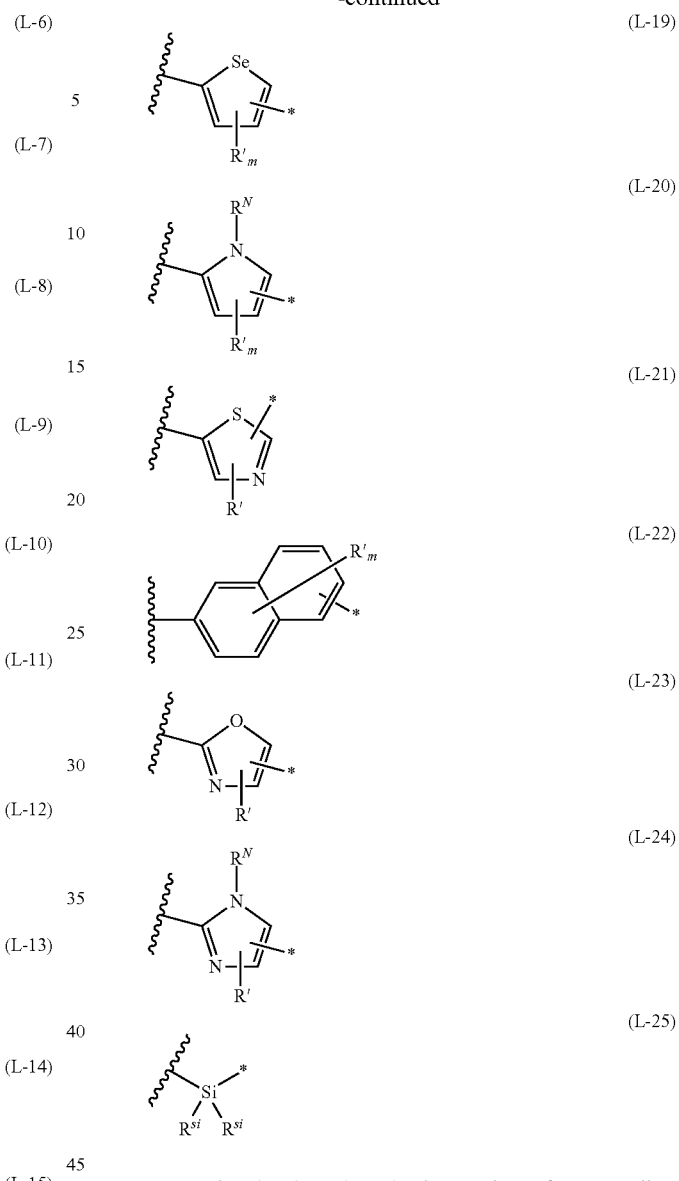

In Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

In Formula (1), each of $R^1$ to $R^8$ independently represents a hydrogen atom or a substituent, and at least one of $R^1$, $R^2$, $R^3$, $R^4$, $R^5$, $R^6$, $R^7$, or $R^8$ represents a group represented by Formula (W).

Examples of the substituent that each of $R^1$ to $R^8$ in Formula (1) can independently represent include a halogen atom, an alkyl group (including an alkyl group having 1 to 40 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, or a pentadecyl group; here, the alkyl group also includes a 2,6-dimethyloctyl group, a 2-decyltetradecyl group, a 2-hexyldodecyl group, a group, a 2-butyldecyl group, a 1-octylnonyl group, a 2-octyltetradecyl group, a 2-ethylhexyl group, a cycloalkyl group, a bicycloalkyl group, a tricycloalkyl group, and the like), an alkenyl group (including a 1-pentenyl group, a cycloalkenyl group, a bicycloalkenyl group, and the like), an alkynyl group (including a 1-pentynyl group, a trimethylsilylethynyl group, a triethylsilylethynyl group, a tri-i-propylsilylethynyl group, a 2-p-propylphenylethynyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, a 3,4-diheptoxyphenyl group, and the like), a hetero ring group (may be referred to as a heterocyclic group as well, including a 2-hexylfuranyl group and the like), a cyano group, a hydroxyl group, a nitro group, an acyl group (including a hexanoyl group, a benzoyl group, and the like), an alkoxy group (including a butoxy group and the like), an aryloxy group, a silyloxy group, a heterocyclic oxy group, an acyloxy group, a carbamoyloxy group, an amino group (including an anilino group), an acylamino group, an aminocarbonylamino group (including a ureide group), alkoxy- and aryloxycarbonylamino groups, alkyl- and aryl sulfonylamino groups, a mercapto group, alkyl- and arylthio groups (including a methylthio group, an octylthio group, and the like), a heterocyclic thio group, a sulfamoyl group, a sulfo group, alkyl- and aryl sulfinyl groups, alkyl- and aryl sulfonyl groups, alkyloxy- and aryloxycarbonyl groups, a carbamoyl group, aryl- and heterocyclic azo group, an imide group, a phosphino group, a phosphinyl group, a phosphinyloxy group, a phosphinylamino group, a phosphono group, a silyl group (a ditrimethylsiloxy methylbutoxy group), a hydrazino group, a ureide group, a boronic acid group ($-B(OH)_2$), a phosphate group ($-OPO(OH)_2$), a sulfate group ($-OSO_3H$), and other known substituents.

These substituents may further have the above substituents. In addition, in a case where the compound represented by Formula (1) is a polymer compound having a repeating structure, each of $R^1$ to $R^8$ may have a group derived from a polymerizable group.

Among these, as the substituent that each of $R^1$ to $R^8$ can independently represent, an alkyl group, an aryl group, an alkenyl group, an alkynyl group, a heterocyclic group, an alkoxy group, an alkylthio group, and a group represented by Formula (W) which will be described later are preferable; an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, and a group represented by Formula (W) which will be described later are more preferable; a group having a linking group chain length, which will be described later, of equal to or less than 3.7 Å and a group represented by Formula (W) which will be described later are particularly preferable; and a group represented by Formula (W) which will be described later is more particularly preferable.

The group represented by Formula (W) will be described.

-L-R    Formula (W)

In Formula (W), L represents a divalent linking group represented by any of the following Formulae (L-1) to (L-25) or a divalent linking group in which two or more divalent linking groups represented by any of the following Formulae (L-1) to (L-25), R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group:

(L-1)

(L-2)

(L-3)

(L-4)

(L-5)

(L-6)

(L-7)

(L-8)

(L-9)

(L-10)

(L-11)

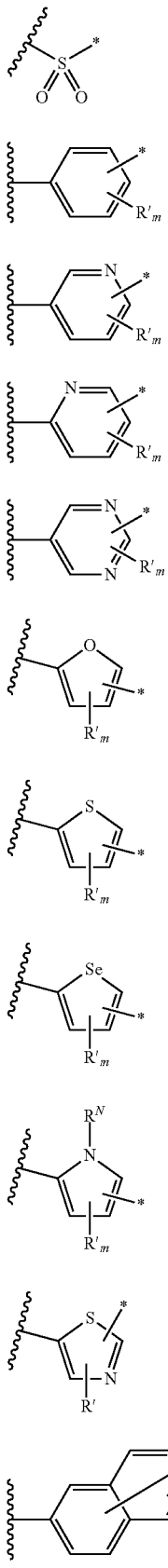

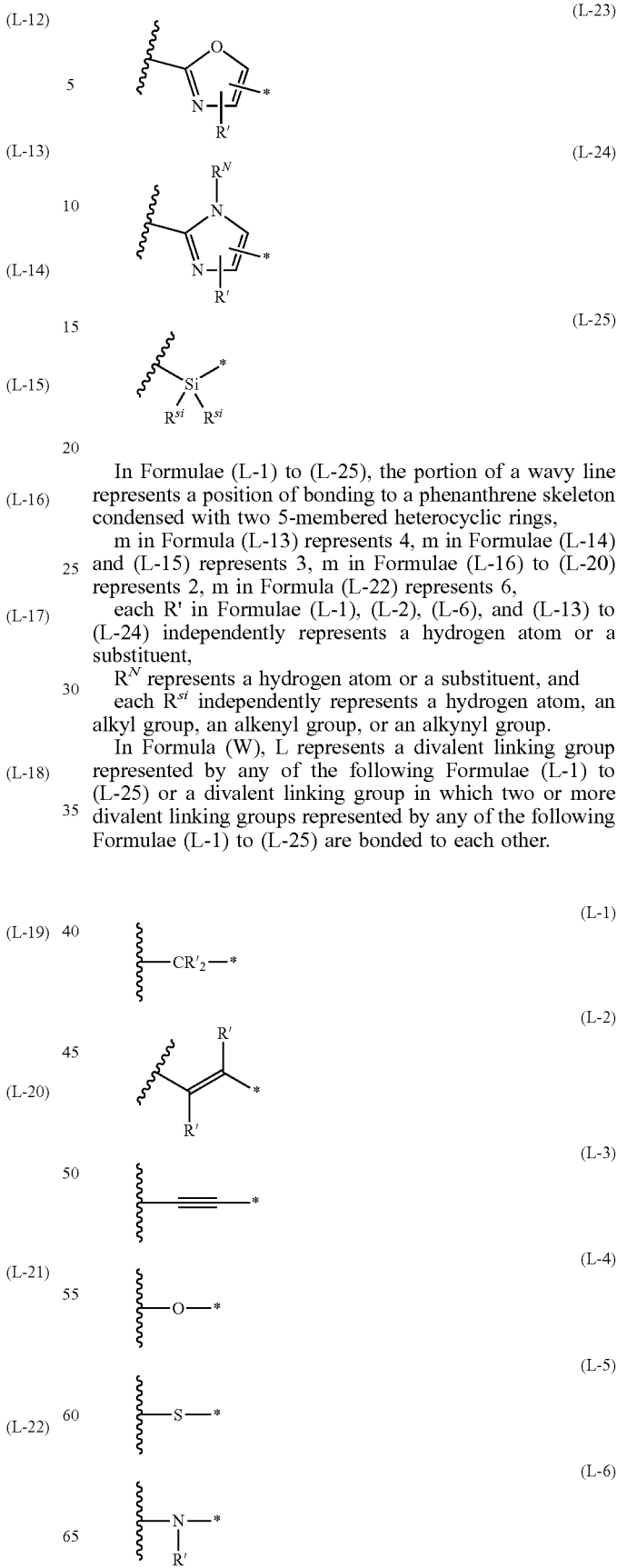

In Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

In Formula (W), L represents a divalent linking group represented by any of the following Formulae (L-1) to (L-25) or a divalent linking group in which two or more divalent linking groups represented by any of the following Formulae (L-1) to (L-25) are bonded to each other.

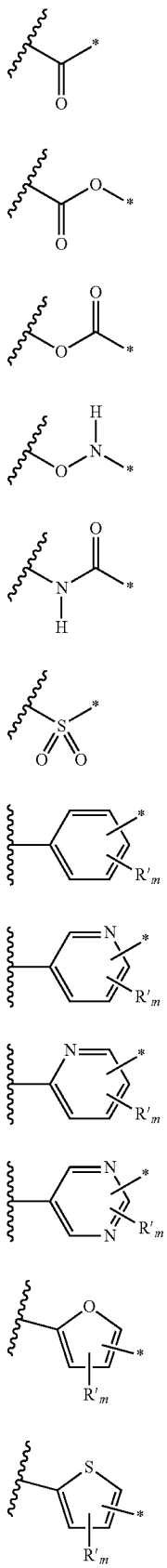

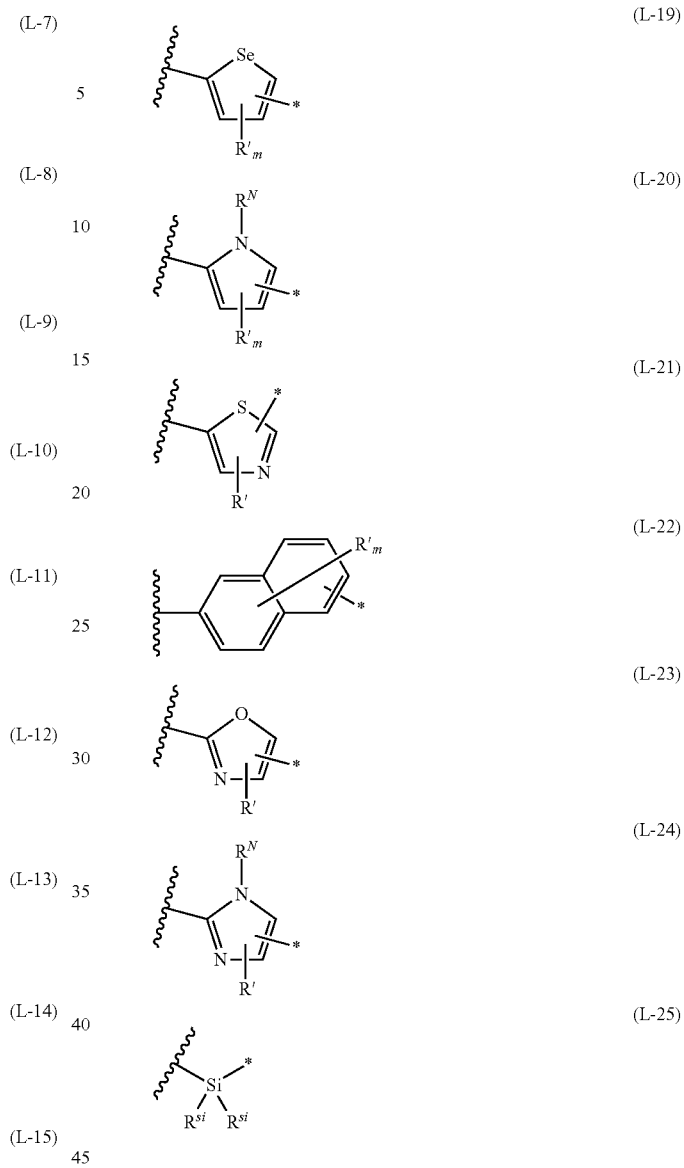

In Formulae (L-1) to (L-25), the portion of a wavy line represents a position of bonding to a phenanthrene skeleton condensed with two 5-membered heterocyclic rings. In the present specification, in a case where L represents a divalent linking group in which two or more divalent linking groups represented by any of Formulae (L-1) to (L-25) are bonded to each other, the portion of wavy line may represents any of a position of bonding to a phenanthrene skeleton condensed with two 5-membered heterocyclic rings or a position of bonding to any of divalent linking groups represented by Formulae (L-1) to (L-25).

* represents a position of bonding to either the divalent linking group represented by any of Formulae (L-1) to (L-25) or R.

m in Formula (L-13) represents 4, m in Formulae (L-14) and (L-15) represents 3, m in Formulae (L-16) to (L-20) represents 2, and m in Formula (L-22) represents 6.

Each R' in Formulae (L-1), (L-2), (L-6), and (L-13) to (L-24) independently represents a hydrogen atom or a substituent.

$R^N$ represents a hydrogen atom or a substituent.

Each $R^{si}$ independently represents a hydrogen atom, an alkyl group, an alkenyl group, or an alkynyl group.

Each R' in Formulae (L-1) and (L-2) may form a condensed ring by being bonded to R adjacent to L.

Among the above, the divalent linking group represented by any of Formulae (L-17) to (L-21), (L-23), and (L-24) is more preferably a divalent linking group represented by any of the following Formulae (L-17A) to (L-21A), (L-23A), and (L-24A).

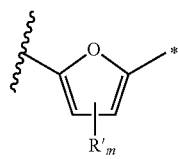
(L-17A)

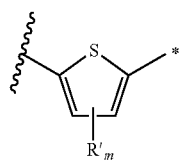
(L-18A)

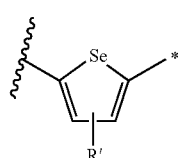
(L-19A)

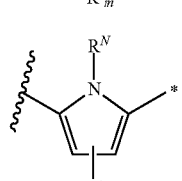
(L-20A)

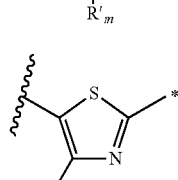
(L-21A)

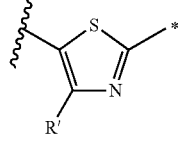
(L-23A)

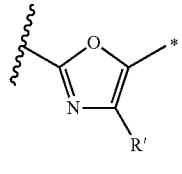
(L-24A)

In a case where a substituted or unsubstituted alkyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group is present on the terminal of the substituent, the substituent can be interpreted as either a substituent consisting of only —R in Formula (W) or a substituent consisting of —R-L in Formula (W).

In the present invention, in a case where a substituted or unsubstituted alkyl group whose main chain consists of N carbon atoms is present on the terminal of the substituent, the substituent is interpreted as -L-R in Formula (W) including linking groups as much as possible from the terminal of the substituent but is not interpreted as a substituent consisting of only —R in Formula (W). Specifically, the substituent is interpreted as a substituent in which "one (L-1) corresponding to L in Formula (W)" is bonded to "a substituted or unsubstituted alkyl group corresponding to R in Formula (W) having a main chain consisting of (N–1) carbon atoms". For example, in a case where a n-octyl group as an alkyl group having 8 carbon atoms is present on the terminal of the substituent, the substituent is interpreted as a substituent in which one (L-1), wherein two R's are hydrogen atoms, is boned to a n-heptyl group having 7 carbon atoms. Furthermore, in a case where the substituent represented by Formula (W) is an alkoxy group having 8 carbon atoms, it is interpreted as a substituent in which one linking group represented by Formula (L-4) which is —O—, one linking group represented by (L-1) in which two R's represent hydrogen atoms, and a n-heptyl group having 7 carbon atoms are bonded to each other.

In contrast, in the present invention, in a case where an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group is present on the terminal of the substituent, the substituent is interpreted as a substituent consisting of only R in Formula (W) including linking groups as much as possible from the terminal of the substituent. For example, in a case where a —(OCH$_2$CH$_2$)—(OCH$_2$CH$_2$)—(OCH$_2$CH$_2$)—OCH$_3$ group is present on the terminal of the substituent, the substituent is interpreted as a substituent consisting of only an oligo-oxyethylene group in which the repetition number v of an oxyethylene unit is 3.

In a case where L forms a linking group in which divalent linking groups represented by any of Formulae (L-1) to (L-25) are bonded to each other, the number of the divalent linking groups bonded to each other represented by any of Formulae (L-1) to (L-25) is preferably 2 to 4, and more preferably 2 or 3.

Examples of the substituent R' in Formulae (L-1), (L-2), (L-6), and (L-13) to (L-24) include those exemplified above as the substituents that can be adopted as $R^1$ to $R^8$ in Formula (1). Among these, the substituent R' in Formula (L-6) is preferably an alkyl group. In a case where R' in (L-6) is an alkyl group, the number of carbon atoms of the alkyl group is preferably 1 to 9, more preferably 4 to 9 from the viewpoint of the chemical stability and the carrier transport properties, and even more preferably 5 to 9. In a case where R' in (L-6) is an alkyl group, the alkyl group is preferably a linear alkyl group because then the carrier mobility can be improved.

$R^N$ represents a hydrogen atom or a substituent, and examples of $R^N$ include those exemplified above as substituents that can be adopted as $R^1$ to $R^8$ in Formula (1) described above. Among these, a hydrogen atom or a methyl group is preferable as $R^N$.

Each $R^{si}$ independently represents a hydrogen atom, an alkyl group, an alkenyl group, or an alkynyl group, and is preferably an alkyl group. The alkyl group that can be adopted as $R^{si}$ is not particularly limited, and the preferred range of the alkyl group that can be adopted as $R^{si}$ is the same as the preferred range of an alkyl group that can be adopted as a silyl group in a case where R is a silyl group. The alkenyl group that can be adopted as $R^{si}$ is not particularly limited. However, the alkenyl group is preferably a substituted or unsubstituted alkenyl group and more preferably a branched alkenyl group, and the number of carbon atoms of the alkenyl group is preferably 2 or 3. The alkynyl group that can be adopted as $R^{si}$ is not particularly limited. However, the alkynyl group is preferably a substituted or unsubstituted alkynyl group and more preferably a branched alkynyl group, and the number of carbon atoms of the alkynyl group is preferably 2 or 3.

L is preferably a divalent linking group represented by any of Formulae (L-1) to (L-5), (L-13), (L-17), and (L-18) or a divalent linking group in which two or more divalent linking groups represented by any of Formulae (L-1) to (L-5), (L-13), (L-17), and (L-18) are bonded to each other, more preferably a divalent linking group represented by any of Formulae (L-1), (L-3), (L-13), and (L-18) or a divalent linking group in which two or more divalent linking groups represented by any of Formulae (L-1), (L-3), (L-13), and (L-18) are bonded to each other, and particularly preferably a divalent linking group represented by (L-1), (L-3), (L-13), or (L-18) or a divalent linking group in which a divalent linking group represented by one of Formulae (L-3), (L-13), and (L-18) is bonded to a divalent linking group represented by Formula (L-1). It is preferable that the divalent linking group represented by Formula (L-1) is bonded to the R side of a divalent linking group in which the divalent linking group represented by any one of Formulae (L-3), (L-13), and (L-18) is bonded to the divalent linking group represented by Formula (L-1).

From the viewpoint of the chemical stability and the carrier transport properties, L is particularly preferably a divalent linking group including the divalent linking group represented by Formula (L-1), more particularly preferably a divalent linking group represented by Formula (L-1). Even more particularly preferably, the substituent represented by (W) is a group in which L represents divalent linking groups represented by Formulae (L-18) and (L-1) and bonded to R through (L-1), and R is a substituted or unsubstituted alkyl group. Still more particularly preferably, the substituent represented by Formula (W) is preferably a group in which L represents divalent linking groups represented by Formulae (L-18A) and (L-1) and bonded to R through (L-1), and R is a substituted or unsubstituted alkyl group.

In Formula (W), R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted silyl group. R is preferably a substituted or unsubstituted alkyl group.

In Formula (W), in a case where L adjacent to R is a divalent linking group represented by Formula (L-1), R is preferably a substituted or unsubstituted alkyl group, an oxyethylene group, an oligo-oxyethylene group in which a repetition number v of an oxyethylene unit is equal to or greater than 2, a siloxane group, or an oligosiloxane group having two or more silicon atoms, and more preferably a substituted or unsubstituted alkyl group.

In Formula (W), in a case where L adjacent to R is a divalent linking group represented by any of Formulae (L-2) and (L-4) to (L-25), R is more preferably a substituted or unsubstituted alkyl group.

In Formula (W), in a case where L adjacent to R is a divalent linking group represented by Formula (L-3), R is preferably a substituted or unsubstituted alkyl group or a substituted or unsubstituted silyl group.

In a case where R is a substituted or unsubstituted alkyl group, the number of carbon atoms thereof is preferably 4 to 17, more preferably 6 to 14 from the viewpoint of the chemical stability and the carrier transport properties, and even more preferably 6 to 12. If R is a long-chain alkyl group within the above range, the alkyl group is particularly preferably a long-chain linear alkyl group because then the linearity of the molecule is improved, and hence the carrier mobility can be improved.

In a case where R represents an alkyl group, the alkyl group may be a linear, branched, or cyclic alkyl group. However, the alkyl group is preferably a linear alkyl group because then the linearity of the molecule is improved, and hence the carrier mobility can be improved.

Among these, from the viewpoint of improving the carrier mobility, R and L in the Formula (W) are preferably combined such that L in Formula (1) is a divalent linking group represented by Formula (L-1), and R is a linear alkyl group having 4 to 17 carbon atoms; or combined such that L is a divalent linking group in which a divalent linking group represented by any one of Formulae (L-3), (L-13), and (L-18) is bonded to a divalent linking group represented by Formula (L-1), and R is a linear alkyl group.

In a case where every L is a divalent linking group represented by Formula (L-1), and all R is a linear alkyl group having 4 to 17 carbon atoms, R is preferably a linear alkyl group having 6 to 14 carbon atoms from the viewpoint of improving the carrier mobility, and particularly preferably a linear alkyl group having 6 to 12 carbon atoms.

In a case where L is a divalent linking group in which a divalent linking group represented by any one of Formulae (L-3), (L-13), and (L-18) is bonded to a divalent linking group represented by Formula (L-1), and R is a linear alkyl group, R is preferably a linear alkyl group having 4 to 17 carbon atoms, more preferably a linear alkyl group having 6 to 14 carbon atoms from the viewpoint of the chemical stability and the carrier transport properties, and particularly preferably a linear alkyl group having 6 to 12 carbon atoms from the viewpoint of improving the carrier mobility.

In contrast, from the viewpoint of improving the solubility in an organic solvent, R is preferably a branched alkyl group.

In a case where R is an alkyl group having a substituent, examples of the substituent include a halogen atom and the like, and the halogen atom is preferably a fluorine atom. In a case where R is an alkyl group having a fluorine atom, a perfluoroalkyl group may be formed by the substitution of all of the hydrogen atoms with the fluorine atom. Here, R is preferably an unsubstituted alkyl group.

In the present specification, in a case where the R is an ethyleneoxy group or an oligo-oxyethylene group in which a repetition number v of an oxyethylene unit is equal to or greater than 2, the "oligo-oxyethylene group" represented by R refers to a group represented by $-(OCH_2CH_2)_vOY$ (the repetition number v of an oxyethylene unit represents an integer of equal to or greater than 2, and Y on the terminal represents a hydrogen atom or a substituent). In a case where Y on the terminal of the oligo-oxyethylene group is a hydrogen atom, the terminal becomes a hydroxy group. The repetition number v of the oxyethylene unit is preferably 2 to 4, and more preferably 2 or 3. It is preferable that the hydroxy group on the terminal of the oligo-oxyethylene group is sealed. That is, it is preferable that Y represents a substituent. In this case, the hydroxy group is preferably sealed with an alkyl group having 1 to 3 carbon atoms. In other words, Y is preferably an alkyl group having 1 to 3 carbon atoms, more preferably a methyl group or an ethyl group, and particularly preferably a methyl group.

In a case where R is a siloxane group or an oligosiloxane group having two or more silicon atoms, the repetition number of the siloxane unit is preferably 2 to 4, and more preferably 2 or 3. Furthermore, it is preferable that hydrogen atoms or alkyl groups are boned to the Si atoms. In a case where alkyl groups are boned to the Si atoms, the number of carbon atoms of each alkyl group is preferably 1 to 3. For example, it is preferable that methyl groups or ethyl groups are bonded to the Si atoms. The same alkyl groups may be bonded to the Si atoms, or different alkyl groups or hydrogen atoms may be bonded to the Si atoms. In addition, all of the siloxane units constituting the oligosiloxane group may be the same as or different from each other, but it is preferable that they are the same as each other.

In a case where L adjacent to R is a divalent linking group represented by Formula (L-3), R is preferably a substituted or unsubstituted silyl group. In a case where R is a substituted or unsubstituted silyl group, a substituted silyl group is preferable as R. The substituent of the silyl group is not particularly limited. However, the substituent is preferably a substituted or unsubstituted alkyl group, and more preferably a branched alkyl group. In a case where R is a trialkylsilyl group, the number of carbon atoms of each alkyl group bonded to the Si atoms is preferably 1 to 3. For example, it is preferable that methyl groups, ethyl groups, or isopropyl groups are bonded to the Si atoms. The same alkyl groups or different alkyl groups may be bonded to the Si atoms. In a case where R is a trialkylsilyl group further having a substituent on the alkyl group, the substituent is not particularly limited.

In Formula (W), the total number of carbon atoms contained in L and R is preferably 5 to 18. If the total number of carbon atoms contained in L and R is equal to or greater than the lower limit of the above range, the carrier mobility is improved, and the driving voltage is reduced. If the total number of carbon atoms contained in L and R is equal to or less than the upper limit of the above range, the solubility in an organic solvent is improved.

The total number of carbon atoms contained in L and R is preferably 5 to 14, more preferably 6 to 14, particularly preferably 6 to 12, and more particularly preferably 8 to 12.

In the compound represented by Formula (1), the number of groups adopted as one of $R^1$ to $R^8$ and represented by Formula (W) is preferably 1 to 4 from the viewpoint of improving the carrier mobility and the solubility in an organic solvent, more preferably 1 or 2, and particularly preferably 2.

The group represented by Formula (W) is positioned in any of $R^1$ to $R^8$ without particular limitation. However, from the viewpoint of improving the carrier mobility and the solubility in an organic solvent, the group is preferably positioned in $R^5$ or $R^6$.

The number of substituents that are adopted as $R^1$ to $R^8$ but other than the substituent represented by Formula (W) is preferably 0 to 4, more preferably 0 to 2, particularly preferably 0 or 1, and more particularly preferably 0.

In a case where each of $R^1$ to $R^8$ is a substituent other than the substituent represented by Formula (W), the substituent as each of $R^1$ to $R^8$ is preferably a group having a linking group chain length of equal to or less than 3.7 Å, more preferably a group having a linking group chain length of 1.0 Å to 3.7 Å, and even more preferably a group having a linking group chain length of 1.0 Å to 2.1 Å.

The linking group chain length refers to a length from a C atom to the terminal of the substituent $R^0$ in a C—$R^0$ bond of the phenanthrene structure. Structural optimization calculation can be performed using a density functional method (Gaussian 03 (Gaussian Inc.)/basis function: 6-31G*, exchange-correlation functional: B3LYP/LANL2DZ). The molecular lengths of typical substituents are 4.6 Å for a propyl group, 4.6 Å for a pyrrole group, 4.5 Å for a propynyl group, 4.6 Å for a propenyl group, 4.5 Å for an ethoxy group, 3.7 Å for a methylthio group, 3.4 Å for an ethenyl group, 3.5 Å for an ethyl group, 3.6 Å for an ethynyl group, 3.3 Å for a methoxy group, 2.1 Å for a methyl group, and 1.0 Å for a hydrogen atom.

In a case where each of $R^1$ to $R^8$ is a substituent other than the substituent represented by Formula (W), each of the substituents as $R^1$ to $R^8$ is preferably independently a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having two or less carbon atoms, and more preferably independently a substituted or unsubstituted alkyl group having 2 or less carbon atoms.

In a case where each of $R^1$ to $R^8$ is a substituent other than the substituent represented by Formula (W), and each of the substituents as $R^1$ to $R^8$ independently represents a substituted alkyl group having 2 or less carbon atoms, examples of the substituent that the alkyl group can have include a cyano group, a fluorine atom, a deuterium atom, and the like, and among these, a cyano group is preferable. In a case where each of $R^1$ to $R^8$ is a substituent other than the substituent represented by Formula (W), the substituted or unsubstituted alkyl group having 2 or less carbon atoms that is represented by the substituent as each of $R^1$ to $R^8$ is preferably a methyl group, an ethyl group, or a methyl group substituted with a cyano group, more preferably a methyl group or a methyl group substituted with a cyano group, and particularly preferably a methyl group substituted with a cyano group.

In a case where each of $R^1$ to $R^8$ is a substituent other than the substituent represented by Formula (W), and each of the substituents as $R^1$ to $R^8$ independently represents a substituted alkynyl group having 2 or less carbon atoms, examples of the substituent that the alkynyl group can have include a deuterium atom and the like. In a case where each of $R^1$ to $R^8$ is a substituent other than the substituent represented by Formula (W), examples of the substituted or unsubstituted alkynyl group having 2 or less carbon atoms that is represented by the substituent as each of $R^1$ to $R^8$ include an ethynyl group and an acetylene group substituted with a deuterium atom, and among these, an ethynyl group is preferable.

In a case where each of $R^1$ to $R^8$ is a substituent other than the substituent represented by Formula (W), and each of the substituents as $R^1$ to $R^8$ independently represents a substituted alkenyl group having 2 or less carbon atoms, examples of the substituent that the alkenyl group can have include a deuterium atom and the like. In a case where each of $R^1$ to $R^8$ is a substituent other than the substituent represented by Formula (W), examples of a substituted or unsubstituted alkenyl group having 2 or less carbon atoms that is represented by the substituent as each of $R^1$ to $R^8$ include an ethenyl group and an ethenyl group substituted with a deuterium atom, and among these, an ethenyl group is preferable.

In a case where each of $R^1$ to $R^8$ is a substituent other than the substituent represented by Formula (W), and each of the substituents as $R^1$ to $R^8$ independently represents a substituted acyl group having 2 or less carbon atoms, examples of the substituent that the acyl group can have include a fluorine atom and the like. In a case where each of $R^1$ to $R^8$ is a substituent other than the substituent represented by Formula (W), examples of a substituted or unsubstituted acyl group having 2 or less carbon atoms that is represented by the substituent as each of $R^1$ to $R^8$ include a formyl group, an acetyl group, and an acetyl group substituted with fluorine, and among these, a formyl group is preferable.

The compound represented by Formula (1) is preferably a compound represented by the following Formula (2-1) or (2-2), and particularly preferably a compound represented by Formula (2-1) from the viewpoint of high mobility.

First, a case where the compound represented by Formula (1) is a compound represented by the following Formula (2-1) will be described.

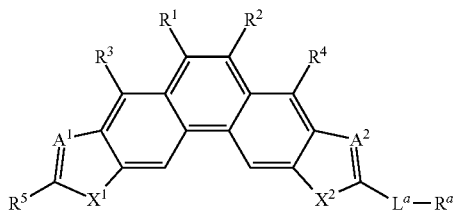

Formula (2-1)

In Formula (2-1), each of $X^1$ and $X^2$ independently represents an O atom or a S atom. The preferred range of $X^1$ and $X^2$ in Formula (2-1) is the same as the preferred range of $X^1$ and $X^2$ in Formula (1).

In Formula (2-1), $A^1$ represents $CR^7$ or a N atom, and $A^2$ represents $CR^8$ or a N atom. Each of $A^1$, $A^2$, $R^7$, and $R^8$ in Formula (2-1) has the same definition as each of $A^1$, $A^2$, $R^7$, and $R^8$ in Formula (1). The preferred range of $A^1$ and $A^2$ in Formula (2-1) is the same as the preferred range of $A^1$ and $A^2$ in Formula (1).

In Formula (2-1), each of $R^1$ to $R^5$, $R^7$, and $R^8$ independently represents a hydrogen atom or a substituent, and $R^5$ is not a group represented by $-L^a-R^a$. In a case where each of $R^1$ to $R^5$, $R^7$, and $R^8$ in Formula (2-1) represents a substituent, the preferred range of the substituent is the same as the preferred range of the substituent that is represented by each of $R^1$ to $R^8$ in Formula (1) and other than the substituent represented by Formula (W).

In Formula (2-1), $L^a$ represents a divalent linking group represented by any of Formulae (L-1) to (L-25) or a divalent linking group in which two or more divalent linking groups represented by any of the following Formulae (L-1) to (L-25) are bonded to each other; and $R^a$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group. The preferred range of $L^a$ and $R^a$ in Formula (2-1) is the same as the preferred range of L and R in Formula (1).

Next, a case where the compound represented by Formula (1) is a compound represented by the following Formula (2-2) will be described.

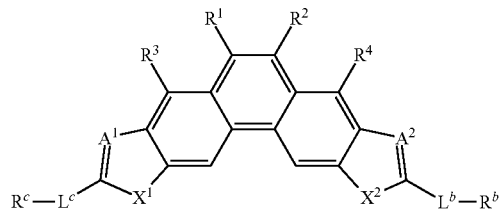

Formula (2-2)

In Formula (2-2), each of $X^1$ and $X^2$ independently represents an O atom or a S atom. The preferred range of $X^1$ and $X^2$ in Formula (2-2) is the same as the preferred range of $X^1$ and $X^2$ in Formula (1).

In Formula (2-2), $A^1$ represents $CR^7$ or a N atom, and $A^2$ represents $CR^8$ or a N atom. Each of $A^1$, $A^2$, $R^7$, and $R^8$ in Formula (2-2) has the same definition as each of $A^1$, $A^2$, $R^7$, and $R^8$ in Formula (1). The preferred range of $A^1$ and $A^2$ in Formula (2-2) is the same as the preferred range of $A^1$ and $A^2$ in Formula (1).

In Formula (2-2), each of $R^1$ to $R^4$, $R^7$, and $R^8$ independently represents a hydrogen atom or a substituent. In a case where each of $R^1$ to $R^4$, $R^7$, and $R^8$ in Formula (2-2) represents a substituent, the preferred range of the substituent is the same as the preferred range of the substituent that is represented by each of $R^1$ to $R^8$ in Formula (1) and other than the substituent represented by Formula (W).

In Formula (2-2), each of $L^b$ and $L^c$ independently represents a divalent linking group represented by any of Formulae (L-1) to (L-25) or a divalent linking group in which two or more divalent linking groups represented by any of Formulae (L-1) to (L-25) are bonded to each other; and each of $R^b$ and $R^c$ independently represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group. The preferred range of $L^b$ and $L^c$ in Formula (2-2) is the same as the preferred range of L in Formula (1), and the preferred range of $R^b$ and $R^c$ in Formula (2-2) is the same as the preferred range of R in Formula (1).

Specific examples of the compound represented by the Formula (1) are shown below, but the compound represented by Formula (1) that can be used in the present invention is not limited to the specific examples.

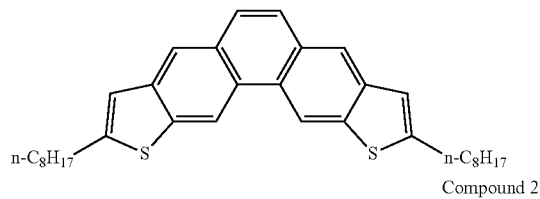

Compound 1

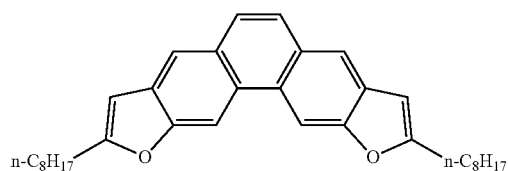

Compound 2

Compound 3
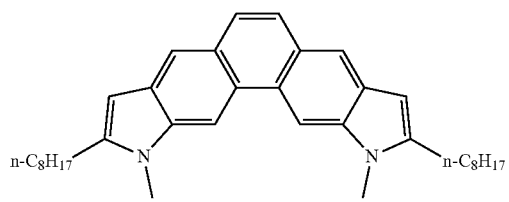
Compound 4
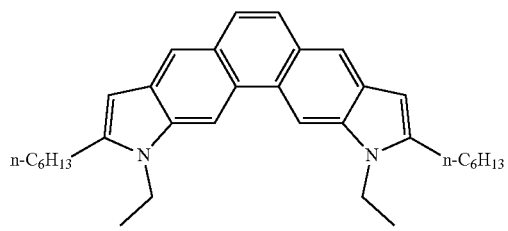
Compound 5
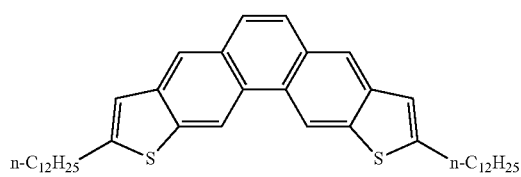
Compound 6
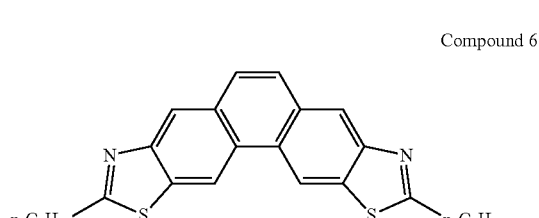
Compound 7
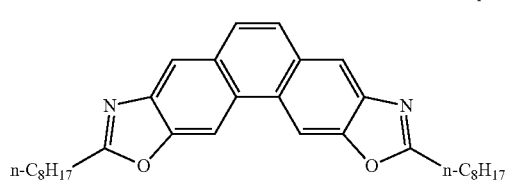
Compound 8
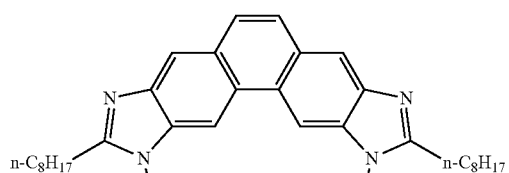
Compound 9
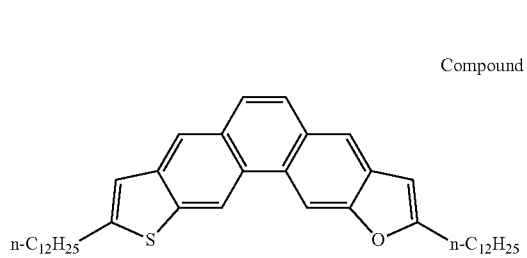
Compound 10
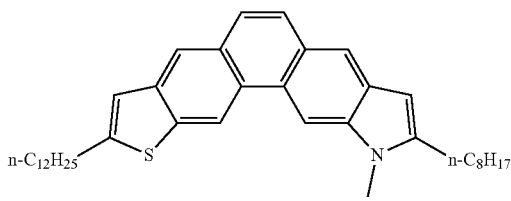
Compound 11
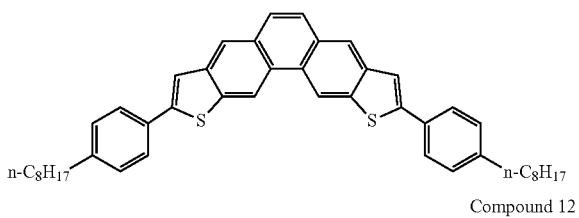
Compound 12
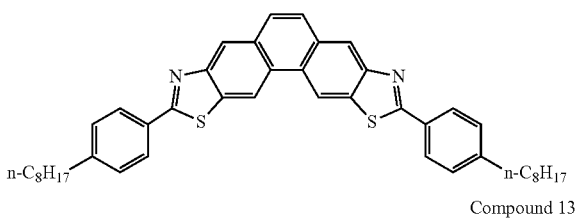
Compound 13
Compound 14
Compound 15
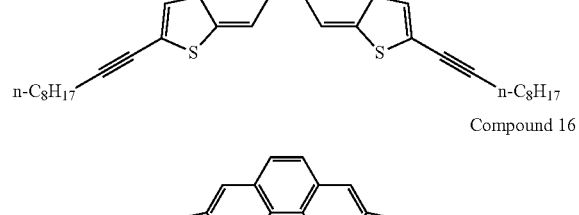
Compound 16
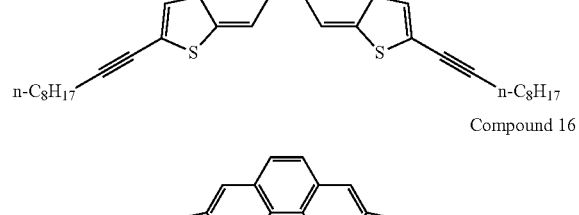
Compound 17
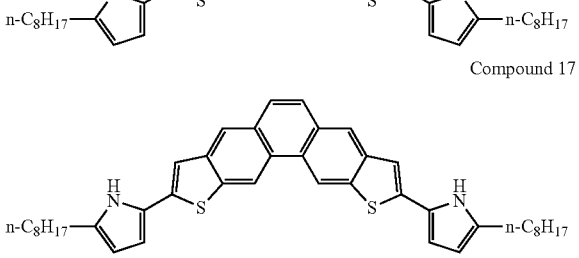

-continued
Compound 18
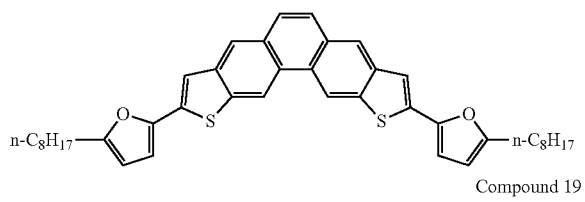
Compound 19
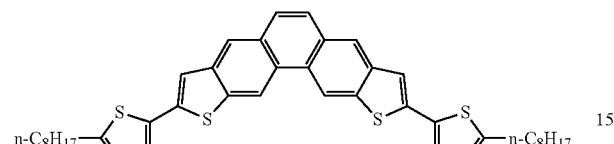
Compound 20
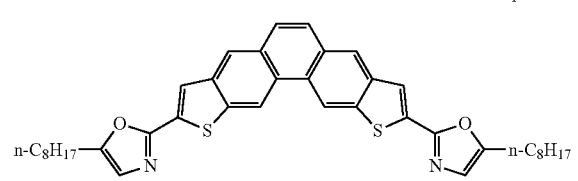
Compound 21
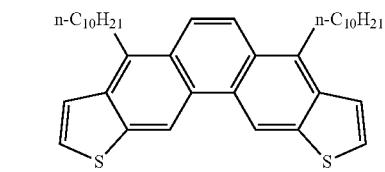
Compound 22
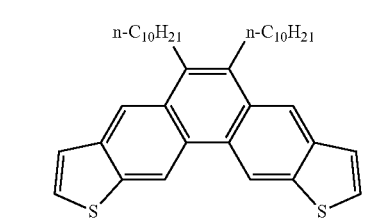
Compound 23
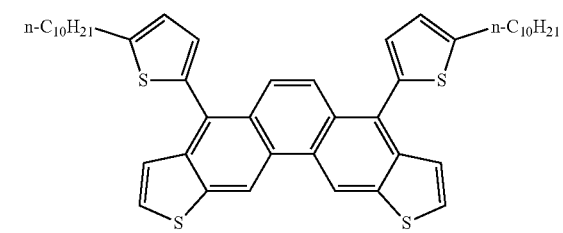
Compound 24
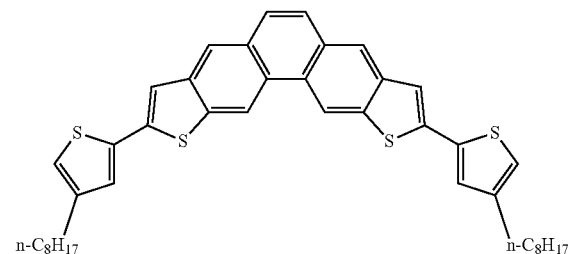
-continued
Compound 25
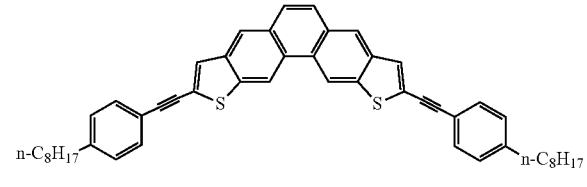
Compound 26
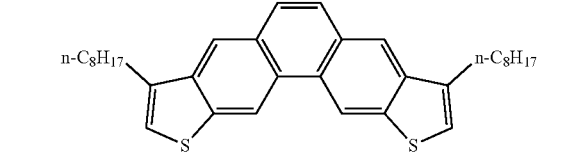
Compound 27
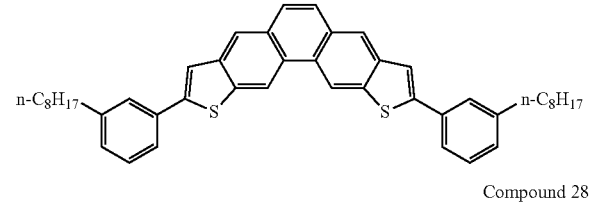
Compound 28
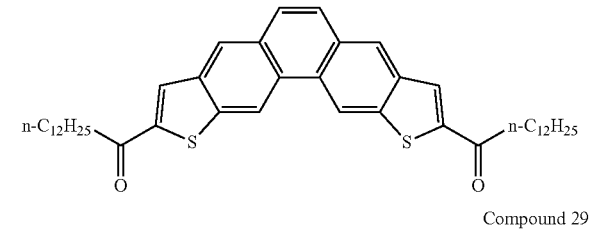
Compound 29
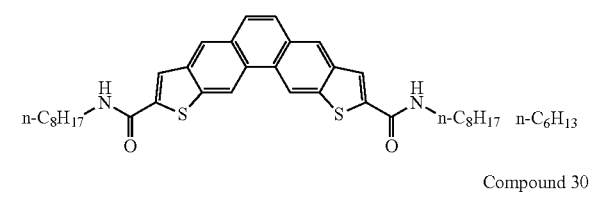
Compound 30
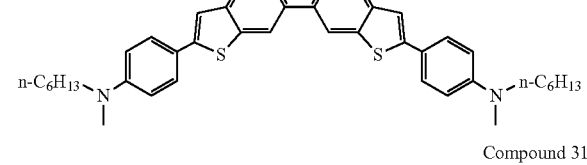
Compound 31
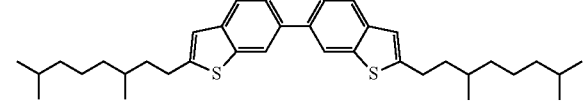
Compound 32
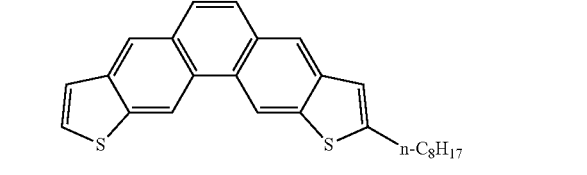

Compound 33

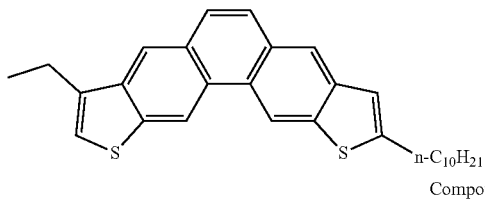

Compound 34

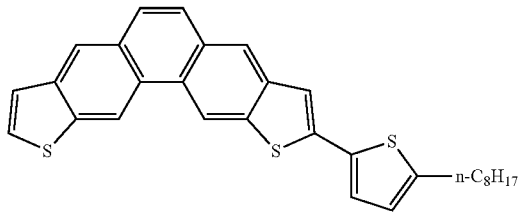

Compound 35

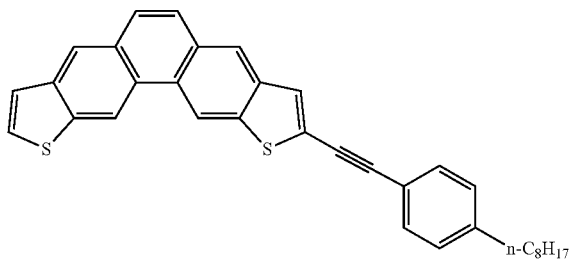

Compound 36

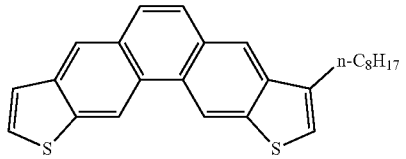

Compound 37

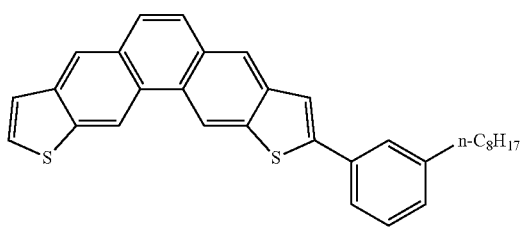

Compound 38

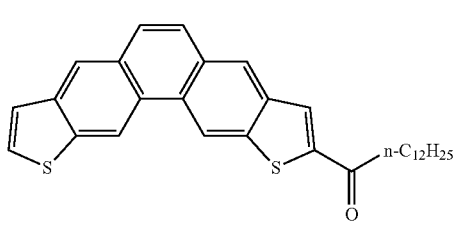

Compound 39

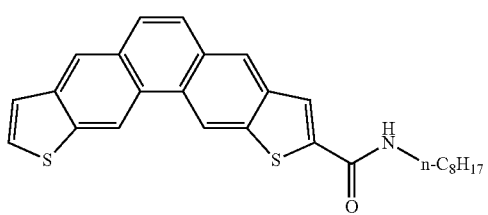

Compound 40

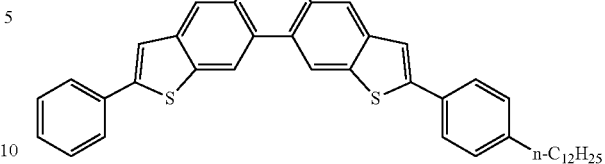

The compound represented by the Formula (1) may have a repeating structure and may be a low-molecular weight compound or a polymer compound. In a case where the compound represented by Formula (1) is a low-molecular weight compound, the molecular weight thereof is preferably equal to or less than 3,000, more preferably equal to or less than 2,000, even more preferably equal to or less than 1,000, and particularly preferably equal to or less than 850. It is preferable that the molecular weight is equal to or less than the upper limit described above because then the solubility in a solvent can be improved.

In contrast, from the viewpoint of the stability of the film quality, the molecular weight is preferably equal to or greater than 400, more preferably equal to or greater than 450, and even more preferably equal to or greater than 500.

Furthermore, in a case where the compound represented by Formula (1) is a polymer compound having a repeating structure, the weight average molecular weight thereof is preferably equal to or greater than 30,000, more preferably equal to or greater than 50,000, and even more preferably equal to or greater than 100,000. In a case where the compound represented by Formula (1) is a polymer compound having a repeating structure, it is preferable that the weight average molecular weight thereof is equal to or greater than the lower limit described above because then the intermolecular interaction can be enhanced, and hence high mobility is obtained.

Examples of the polymer compound having a repeating structure include a π-conjugated polymer having a repeating structure in which the compound represented by Formula (1) represents at least one or more arylene groups or heteroarylene groups (thiophene or bithiophene), and a pendant-type polymer in which the compound represented by Formula (1) is bonded to the main chain of the polymer via the side chain. As the main chain of the polymer, polyacrylate, polyvinyl, polysiloxane, or the like is preferable, and as the side chain, an alkylene group, a polyethylene oxide group, or the like is preferable.

The compound represented by Formula (1) can be synthesized with reference to known documents (J. Org. Chem, 2011, 696, Org. Lett., Org. Lett., 2001, 3, 3471, Macromolecules, 2010, 43, 6264, J. Org. Chem. 2013, 78, 7741, Chem. Eur. J. 2013, 19, 3721) by using, as a starting material, a compound a described in scheme 1 which will be described later.

In synthesizing the compound of the present invention, any of reaction conditions may be used. As a reaction solvent, any solvent may be used. Furthermore, in order to accelerating a ring forming reaction, an acid or a base is preferably used, and a base is particularly preferably used. The optimal reaction conditions vary with the structure of the intended compound, but can be set with reference to the specific reaction conditions described in the above documents.

<Intermediate Compound>

The synthetic intermediate having various substituents can be synthesized using known reactions in combination. Furthermore, various substituents may be introduced into the intermediate at any stage. After the intermediate is synthesized, it is preferable to purify the intermediate by column chromatography, recrystallization, or the like and then further purify it by sublimation. By the sublimation purification, it is possible to separate organic impurities and to effectively remove an inorganic salt, a residual solvent, and the like.

The present invention also relates to a compound represented by the following Formula (3) and a compound represented by the following Formula (4).

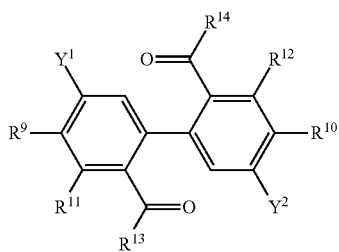

Formula (3)

In Formula (3), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, and each of $R^{11}$ to $R^{14}$ independently represents a hydrogen atom or a substituent.

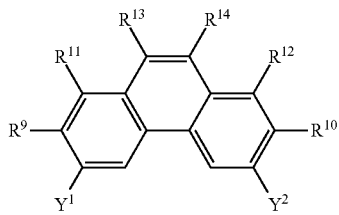

Formula (4)

In Formula (4), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, and each of $R^{11}$ to $R^{14}$ independently represents a hydrogen atom or a substituent.

It is preferable that each of the compound represented by Formula (3) described above and the compound represented by Formula (4) described above is the intermediate compound of the compound represented by Formula (1) described above. The compound represented by Formula (1) described above can be synthesized according to scheme 1, which will be described later, through a process in which the compound represented by Formula (3) described above and the compound represented by Formula (4) described above are synthesized as synthetic intermediate compounds.

In Formulae (3) and (4), each of $Y_1$ and $Y_2$ is a halogen atom. Examples of the halogen atom include a fluorine atom, a chlorine atom, a bromine atom, and an iodine atom, and among these, a fluorine atom is preferable.

In Formulae (3) and (4), each of $R^9$ and $R^{10}$ independently represents a halogen atom, a carbonyl group, a trialkylsilyl group, an alkynyl group, or an alkenyl group. Among these, a halogen atom, a trialkylsilyl group, and an alkenyl group are preferable.

In a case where each of $R^9$ and $R^{10}$ represents a halogen atom, examples of the halogen atom include an iodine atom, a bromine atom, and a chlorine atom, and among these, an iodine atom is preferable.

In a case where each of $R^9$ and $R^{10}$ represents a trialkylsilyl group, the alkyl group linked to the silyl group is preferably an alkyl group having 1 to 4 carbon atoms, and more preferably a methyl group.

In a case where each of $R^9$ and $R^{10}$ represents an alkynyl group, the alkynyl group is preferably an alkynyl group having 1 to 24 carbon atoms, and more preferably an alkynyl group having 1 to 16 carbon atoms.

In a case where each of $R^9$ and $R^{10}$ represents an alkenyl group, the alkenyl group is preferably an alkenyl group having 1 to 24 carbon atoms, and more preferably an alkenyl group having 1 to 16 carbon atoms.

In Formulae (3) and (4), each of $R^{11}$ and $R^{12}$ represents a hydrogen atom or a substituent.

In Formulae (3) and (4), each of $R^{13}$ and $R^{14}$ represents a hydrogen atom or a substituent, and preferably represents a hydrogen atom.

In a case where each of $R^{11}$ to $R^{14}$ in Formulae (3) and (4) independently represents a substituent, the preferred range of the substituent is the same as the preferred range of the substituent represented by Formula (W) and as the preferred range of the substituent that is represented by each of $R^1$ to $R^8$ in Formula (1) and other than the substituent represented by Formula (W).

<Structure of Organic Transistor>

The organic transistor of the present invention has a semiconductor active layer containing the compound represented by Formula (1).

The organic transistor of the present invention may further have layers other than the semiconductor active layer.

The organic transistor of the present invention is preferably used as an organic field effect transistor (FET), and is more preferably used as an insulated gate-type FET in which the gate is insulated from channels.

Hereinafter, preferred structural aspects of the organic transistor of the present invention will be specifically described by using drawings, but the present invention is not limited to the aspects.

(Lamination Structure)

The lamination structure of an organic field effect transistor is not particularly limited, and various known structures can be adopted.

For example, the organic transistor of the present invention can adopt a structure (bottom gate/top contact type) in which an electrode, an insulator layer, a semiconductor active layer (organic semiconductor layer), and two electrodes are arranged in this order on the upper surface of a substrate which is a lower most layer. In this structure, the electrode on the upper surface of the substrate as the lower most layer is provided in a portion of the substrate, and the insulator layer is so disposed that it comes into contact with the substrate in a portion other than the electrode. The two electrodes provided on the upper surface of the semiconductor active layer are arranged in a state of being separated from each other.

FIG. 1 shows the constitution of a bottom gate/top contact-type element. FIG. 1 is a schematic view showing a section of an exemplary structure of the organic transistor of the present invention. In the organic transistor shown in FIG. 1, a substrate 11 is disposed as a lower most layer, an electrode 12 is provided in a portion of the upper surface thereof, and an insulator layer 13 is provided such that it covers the electrode 12 and comes into contact with the substrate 11 in a portion other than the electrode 12. On the upper surface of the insulator layer 13, a semiconductor active layer 14 is provided, and in a portion of the upper surface thereof, two electrodes 15a and 15b separated from each other are arranged.

In the organic transistor shown in FIG. 1, the electrode 12 is a gate, and the electrode 15a and the electrode 15b are a drain and a source respectively. The organic transistor shown in FIG. 1 is an insulated gate-type FET in which a channel as a path of electric currents between the drain and the source is insulated from the gate.

As an example of the structure of the organic transistor of the present invention, a bottom gate/bottom contact-type element can be exemplified.

Figure 2:
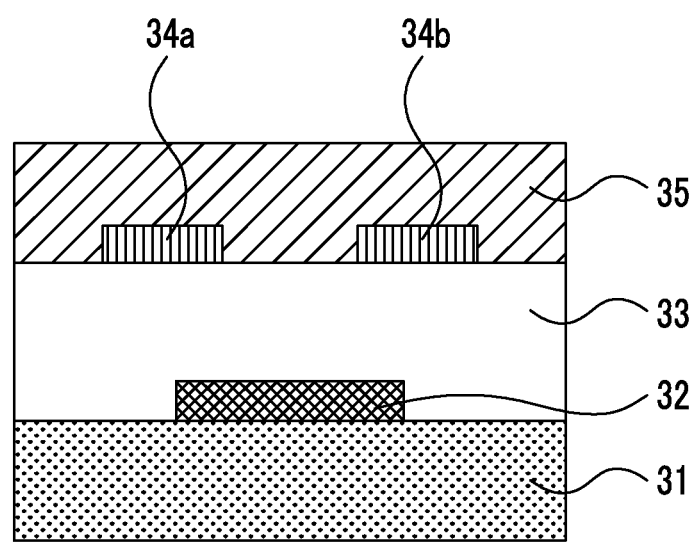
FIG. 2 is a schematic view showing a section of a structure of the organic transistor manufactured as a substrate for measuring FET characteristics in examples of the present invention.

FIG. 2 shows the constitution of the bottom gate/bottom contact-type element. FIG. 2 is a schematic view showing a section of the structure of an organic transistor manufactured as a substrate for measuring FET characteristics in examples of the present invention. In the organic transistor shown in FIG. 2, a substrate 31 is disposed as a lower most layer, an electrode 32 is provided in a portion of the upper surface thereof, and an insulator layer 33 is provided such that it covers the electrode 32 and comes into contact with the substrate 31 in a portion other than the electrode 32. Furthermore, a semiconductor active layer 35 is provided on the upper surface of the insulator layer 33, and electrodes 34a and 34b are in a lower portion of the semiconductor active layer 35.

In the organic transistor shown in FIG. 2, the electrode 32 is a gate, and the electrode 34a and the electrode 34b are a drain and a source respectively. The organic transistor shown in FIG. 2 is an insulated gate-type FET in which a channel as a path of electric currents between the drain and the source is insulated from the gate.

As the structure of the organic transistor of the present invention, a top gate/top contact-type element in which an insulator and a gate electrode are in the upper portion of a semiconductor active layer or a top gate/bottom contact-type element can also be preferably used.

(Thickness)

In a case where the organic transistor of the present invention needs to be a thinner transistor, the total thickness of the transistor is preferably, for example, 0.1 µm to 0.5 µm.

(Sealing)

In order to improve the preservation stability of the organic transistor element by blocking the organic transistor element from the atmosphere or moisture, the entirety of the organic transistor element may be sealed with a metal sealing can, glass, an inorganic material such as silicon nitride, a polymer material such as parylene, a low-molecular weight material, or the like.

Hereinafter, preferred aspects of the respective layers of the organic transistor of the present invention will be described, but the present invention is not limited to the aspects.

<Substrate>

(Material)

The organic transistor of the present invention preferably includes a substrate.

The material of the substrate is not particularly limited, and known materials can be used. Examples of the material include a polyester film such as polyethylene naphthalate (PEN) or polyethylene terephthalate (PET), a cycloolefin polymer film, a polycarbonate film, a triacetylcellulose (TAC) film, a polyimide film, a material obtained by bonding these polymer films to extremely thin glass, ceramics, silicon, quartz, glass, and the like. Among these, silicon is preferable.

<Electrode>

(Material)

The organic transistor of the present invention preferably includes an electrode.

As the material constituting the electrode, known conductive materials such as a metal material like Cr, Al, Ta, Mo, Nb, Cu, Ag, Au, Pt, Pd, In, Ni, or Nd, an alloy material of these, a carbon material, and a conductive polymer can be used without particular limitation.

(Thickness)

The thickness of the electrode is not particularly limited, but is preferably 10 nm to 50 nm.

A gate width (or a channel width) W and a gate length (or a channel length) L are not particularly limited. However, a ratio of W/L is preferably equal to or greater than 10, and more preferably equal to or greater than 20.

<Insulator Layer>

(Material)

The material constituting the insulator layer is not particularly limited as long as an insulating effect is obtained as required. Examples of the material include silicon dioxide, silicon nitride, a fluorine polymer-based insulating material such as PTFE or CYTOP, a polyester insulating material, a polycarbonate insulating material, an acryl polymer-based insulating material, an epoxy resin-based insulating material, a polyimide insulating material, a polyvinyl phenol resin-based insulating material, a poly p-xylylene resin-based insulating material, and the like.

A surface treatment may be performed on the upper surface of the insulator layer. For example, it is possible to preferably use an insulator layer in which the silicon dioxide surface thereof is subjected to the surface treatment by being coated with hexamethyldisilazane (HMDS) or octadecyl-trichlorosilane (OTS).

(Thickness)

The thickness of the insulator layer is not particularly limited. However, in a case where the film needs to be thinned, the thickness of the insulating layer is preferably 10 nm to 400 nm, more preferably 20 nm to 200 nm, and particularly preferably 50 nm to 200 nm.

<Semiconductor Active Layer>

(Material)

In the organic transistor of the present invention, the semiconductor active layer contains a compound represented by Formula (1) described above, that is, the compound of the present invention.

The semiconductor active layer may be a layer consisting of the compound of the present invention or a layer further containing a polymer binder, which will be described later, in addition to the compound of the present invention. Furthermore, the semiconductor active layer may contain a residual solvent used at the time of forming a film.

The content of the polymer binder in the semiconductor active layer is not particularly limited. However, the content of the polymer binder is preferably within a range of 0% by mass to 95% by mass, more preferably within a range of 10% by mass to 90% by mass, even more preferably within a range of 20% by mass to 80% by mass, and particularly preferably within a range of 30% by mass to 70% by mass.

(Thickness)

The thickness of the semiconductor active layer is not particularly limited. However, in a case where the film needs to be thinned, the thickness of the semiconductor active layer is preferably 10 nm to 400 nm, more preferably 10 nm to 200 nm, and particularly preferably 10 nm to 100 nm.

[Organic Semiconductor Material for Non-Light-Emitting Organic Semiconductor Device]

The present invention also relates to an organic semiconductor material for a non-light-emitting organic semiconductor device containing the compound represented by Formula (1), that is, the compound of the present invention.

(Non-Light-Emitting Organic Semiconductor Device)

In the present specification, a "non-light-emitting organic semiconductor device" refers to a device which is not used for the purpose of emitting light. The non-light-emitting organic semiconductor device preferably uses an electronic element having a layered structure consisting of films. The non-light-emitting organic semiconductor device includes an organic transistor, an organic photoelectric conversion element (a solid-state imaging element used for a photosensor, a solar cell used for energy conversion, or the like), a gas sensor, an organic rectifying element, an organic inverter, an information recording element, and the like. The organic photoelectric conversion element can be used for both a photosensor (solid-state imaging element) and for energy conversion (a solar cell). Among these, an organic photoelectric conversion element and an organic transistor are preferable, and an organic transistor is more preferable. That is, the organic semiconductor material for a non-light-emitting organic semiconductor device of the present invention is preferably a material for an organic transistor as described above.

(Organic Semiconductor Material)

In the present specification, the "organic semiconductor material" is an organic material showing characteristics of a semiconductor. Just as the semiconductor composed of an inorganic material, the organic semiconductor is classified into a p-type (hole-transporting) organic semiconductor material conducting holes as carriers and an n-type (electron-transporting) organic semiconductor material conducting electrons as carriers.

The compound of the present invention may be used as any of the p-type organic semiconductor material and the n-type organic semiconductor material, but is preferably used as the p-type. The ease with which the carriers flow in the organic semiconductor is represented by a carrier mobility $\mu$. The higher the carrier mobility $\mu$, the better. The carrier mobility $\mu$ is preferably equal to or greater than $1\times10^{-4}$ cm$^2$/Vs, more preferably equal to or greater than $1\times10^{-3}$ cm$^2$/Vs, particularly preferably equal to or greater than $5\times10^{-3}$ cm$^2$/Vs, and more particularly preferably equal to or greater than $1\times10^{-2}$ cm$^2$/Vs, and even more particularly preferably equal to or greater than $5\times10^{-2}$ cm$^2$/Vs. The carrier mobility $\mu$ can be determined by the characteristics of the prepared field effect transistor (FET) element or by a time-of-flight (TOF) measurement method.

[Organic Semiconductor Film for Non-Light-Emitting Organic Semiconductor Device]

(Material)

The present invention also relates to an organic semiconductor film for a non-light-emitting organic semiconductor device containing the compound represented by Formula (1), that is, the compound of the present invention.

As the organic semiconductor film for a non-light-emitting organic semiconductor device of the present invention, an aspect is also preferable in which the organic semiconductor film contains the compound represented by Formula (1), that is, the compound of the present invention, and does not contain a polymer binder.

Furthermore, the organic semiconductor film for a non-light-emitting organic semiconductor device of the present invention may contain the compound represented by Formula (1), that is, the compound of the present invention, and a polymer binder.

Examples of the polymer binder include an insulating polymer such as polystyrene, polycarbonate, polyarylate, polyester, polyamide, polyimide, polyurethane, polysiloxane, polysulfone, polymethyl methacrylate, polymethyl acrylate, cellulose, polyethylene, or polypropylene, a copolymer of these, a photoconductive polymer such as polyvinylcarbazole or polysilane, a conductive polymer such as polythiophene, polypyrrole, polyaniline, or poly p-phenylenevinylene, and a semiconductor polymer.

One kind of the aforementioned polymer binder may be used singly, or plural kinds thereof may be used concurrently.

The organic semiconductor material may be uniformly mixed with the polymer binder. Alternatively, the organic semiconductor material and the polymer binder may be totally or partially in a phase separation state. From the viewpoint of the charge mobility, a structure, in which the organic semiconductor and the binder are in a phase separation state along the film thickness direction in the film, is the most preferable because then the binder does not hinder the organic semiconductor from moving a charge.

Considering the mechanical strength of the film, a polymer binder having a high glass transition temperature is preferable. Furthermore, considering the charge mobility, a polymer binder having a structure not containing a polar group, a photoconductive polymer, and a conductive polymer are preferable.

The amount of the polymer binder used is not particularly limited. However, in the organic semiconductor film for a non-light-emitting organic semiconductor device of the present invention, the amount of the polymer binder used is preferably within a range of 0% by mass to 95% by mass, more preferably within a range of 10% by mass to 90% by mass, even more preferably within a range of 20% by mass to 80% by mass, and particularly preferably within a range of 30% by mass to 70% by mass.

In the present invention, by adopting the aforementioned structure as the structure of the compound, a film having excellent quality can be obtained. Specifically, because the compound obtained in the present invention has excellent crystallinity, a sufficient film thickness can be obtained, and the obtained organic semiconductor film for a non-light-emitting organic semiconductor device of the present invention has excellent quality.

(Film Forming Method)

The compound of the present invention may be formed into a film on a substrate by any method.

At the time of forming the film, the substrate may be heated or cooled. By varying the temperature of the substrate, it is possible to control the film quality or the packing of molecules in the film. The temperature of the substrate is not particularly limited. However, it is preferably between 0° C. to 200° C., more preferably between 15° C. to 100° C., and particularly preferably between 20° C. to 95° C.

The compound of the present invention can be formed into a film on a substrate by a vacuum process or a solution process, and both of the processes are preferable.

Specific examples of the film forming method by a vacuum process include a physical vapor deposition method such as a vacuum vapor deposition method, a sputtering method, an ion plating method, or a molecular beam epitaxy (MBE) method and a chemical vapor deposition (CVD) method such as plasma polymerization, and it is particularly preferable to use a vacuum vapor deposition method.

Herein, the film forming method by a solution process refers to a method of dissolving an organic compound in a solvent which can dissolve the compound and forming a film by using the solution. Specifically, it is possible to use general methods like a coating method such as a casting method, a dip coating method, a die coater method, a roll coater method, a bar coater method, or a spin coating method, various printing methods such as an ink jet method, a screen printing method, a gravure printing method, a flexographic printing method, an offset printing method, or a micro-contact printing method, and a Langmuir-Blodgett (LB) method. It is particularly preferable to use a casting method, a spin coating method, an ink jet method, a gravure printing method, a flexographic printing method, an offset printing method, or a micro-contact printing method.

The organic semiconductor film for a non-light-emitting organic semiconductor device of the present invention is preferably prepared by a solution coating method. In a case where the organic semiconductor film for a non-light-emitting organic semiconductor device of the present invention contains a polymer binder, it is preferable to prepare a coating solution by dissolving or dispersing a material, which will be formed into a layer, and a polymer binder in an appropriate solvent and to form the organic semiconductor film by various coating methods.

Hereinafter, a coating solution for a non-light-emitting organic semiconductor device of the present invention that can be used for forming a film by a solution process will be described.

[Coating Solution for Non-Light-Emitting Organic Semiconductor Device]

The present invention also relates to a coating solution containing the compound represented by Formula (1), that is a coating solution for a non-light-emitting organic semiconductor device containing the compound of the present invention.

In a case where a film is formed on a substrate by using a solution process, a material which will be formed into a layer is dissolved or dispersed in either or both of an appropriate organic solvent (for example, a hydrocarbon-based solvent such as hexane, octane, decane, toluene, xylene, mesitylene, ethylbenzene, decalin, or 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, dichloroethane, trichloroethane, tetrachloroethane, chlorobenzene, dichlorobenzene, or chlorotoluene, an ester-based solvent such as ethyl acetate, butyl acetate, or amyl acetate, an alcohol-based solvent such as methanol, propanol, butanol, pentanol, hexanol, cyclohexanol, methyl cellosolve, ethyl cellosolve, or ethylene glycol, an ether-based solvent such as dibutylether, tetrahydrofuran, dioxane, or anisole, an amide.imide-based solvent such as N,N-dimethylformamide, N,N-dimethylacetamide, 1-methyl-2-pyrrolidone, or 1-methyl-2-imidazolidinone, a sulfoxide-based solvent such as dimethyl sulfoxide, or a nitrile-based solvent such as acetonitrile) and water so as to obtain a coating solution, and a film can be formed by various coating methods by using the coating solution. One kind of the solvent may be used singly, or plural kinds thereof may be used in combination. Among these, a hydrocarbon-based solvent, a halogenated hydrocarbon-based solvent, and an ether-based solvent are preferable, toluene, xylene, mesitylene, tetralin, dichlorobenzene, and anisole are more preferable, and toluene, xylene, tetralin, and anisole are particularly preferable. The concentration of the compound represented by Formula (1) in the coating solution is preferably 0.1% by mass to 80% by mass, more preferably 0.1% by mass to 10% by mass, and particularly preferably 0.5% by mass to 10% by mass. In this way, a film having an arbitrary thickness can be formed.

In order to form a film by a solution process, the material needs to dissolve in the solvent exemplified above, but simply dissolving in a solvent is not good enough. Generally, even the material formed into a film by a vacuum process can dissolve in a solvent to some extent. The solution process includes a step of coating a substrate with a material by dissolving the material in a solvent and then forming a film by evaporating the solvent, and many of the materials not suitable for being formed into a film by the solution process have high crystallinity. Therefore, the material is inappropriately crystallized (aggregated) in the aforementioned step, and hence it is difficult to form an excellent film. The compound represented by Formula (1) is also excellent in the respect that it is not easily crystallized (aggregated).

As the coating solution for a non-light-emitting organic semiconductor device of the present invention, an aspect is also preferable in which the coating solution contains the compound represented by Formula (1), that is, the compound of the present invention, and does not contain a polymer binder.

Furthermore, the coating solution for a non-light-emitting organic semiconductor device of the present invention may contain the compound represented by Formula (1), that is, the compound of the present invention, and a polymer binder. In this case, a material, which will be formed into a layer, and a polymer binder are dissolved or dispersed in an appropriate solvent described above so as to prepare a coating solution, and by using the coating solution, a film can be formed by various coating methods. The polymer binder can be selected from those described above.

EXAMPLES

Hereinafter, the characteristics of the present invention will be more specifically explained by describing examples and comparative examples. The materials, the amount thereof used, the proportion thereof, the content of treatment, the treatment procedure, and the like described in the following examples can be appropriately modified within a range that does not depart from the gist of the present invention. Accordingly, the scope of the present invention is not limited to the following specific examples.

Example 1

<Synthesis Example 1> Synthesis of Compounds 1 to 3, 5, 11, 13, 15, 16, and 24 and Intermediate Compounds c, d, e, and f According to a specific synthesis procedure shown in the following scheme 1, compounds 1 to 3, 5, 11, 13, 15, 16, and 24 as the compound represented by Formula (1) and intermediate compounds c, d, e, and f were synthesized.

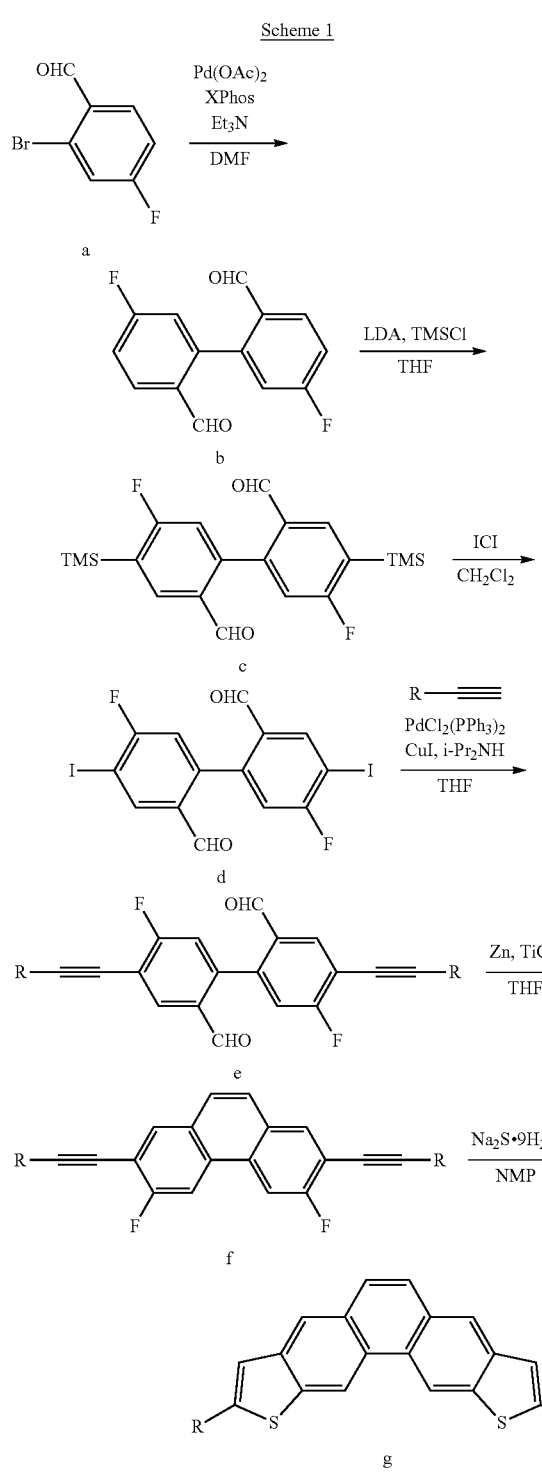

(Synthesis of Compound c)

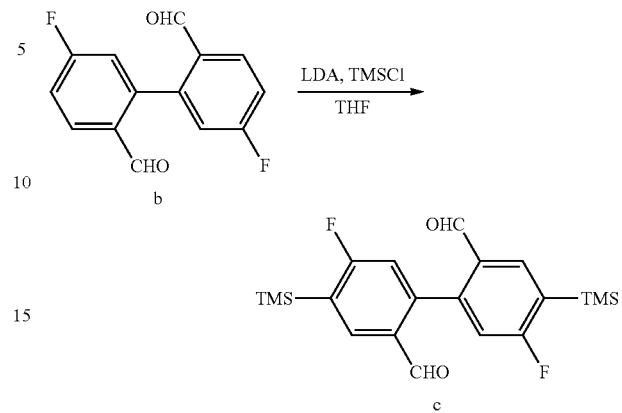

The compound c can be synthesized with reference to US2008/45511A.

The structure of the compound c was identified by $^1$H-NMR.

(Synthesis of Compound d)

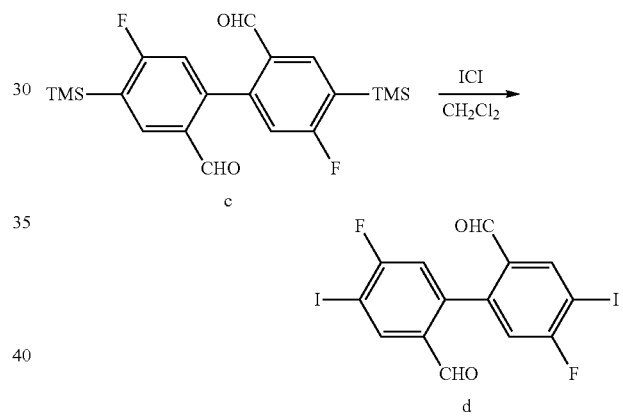

The compound d can be synthesized with reference to a known document (Org. Lett., 2001, 3, 3471).

The structure of the compound d was identified by $^1$H-NMR.

(Synthesis of Compound E)

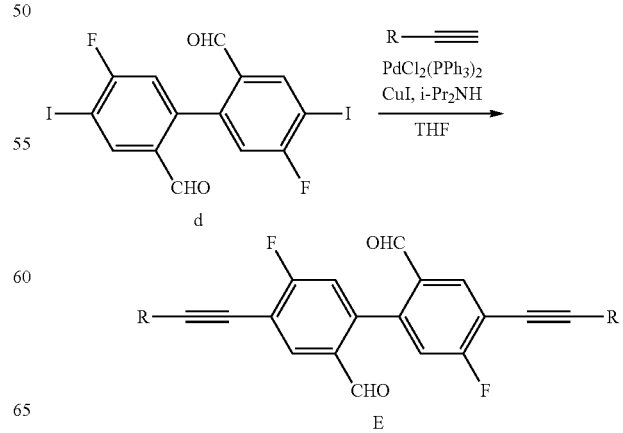

A process will be specifically described in which the intermediate compounds c represented by Formula (3), the intermediate compounds d and E, the intermediate compound F represented by Formula (4), and then the compound represented by Formula (1) are synthesized from the following intermediate compound b.

The compound E in which every R in the intermediate compound e shown in the above scheme 1 represents a n-octyl group was synthesized.

The compound E can be synthesized with reference to a know document (Tetrahedron. Lett., 1996, 37, 7901).

The structure of the compound E was identified by $^1$H-NMR.

(Synthesis of Compound F)

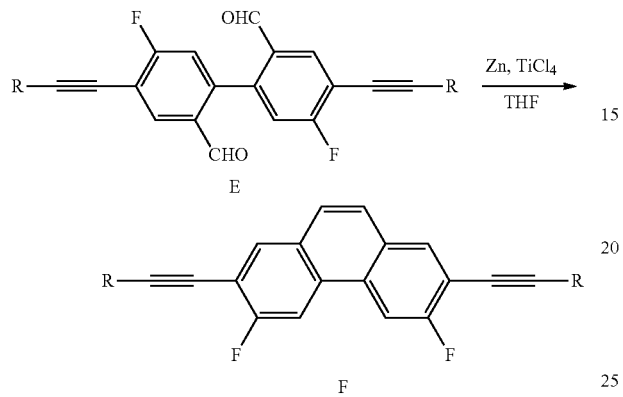

The compound F in which every R in the intermediate compound f shown in the above scheme 1 represents a n-octyl group was synthesized.

The compound F can be synthesized with reference to a known document (Tetrahedron. Lett., 2006, 47, 1221).

The structure of the compound F was identified by $^1$H-NMR.

(Synthesis of Compound 1)

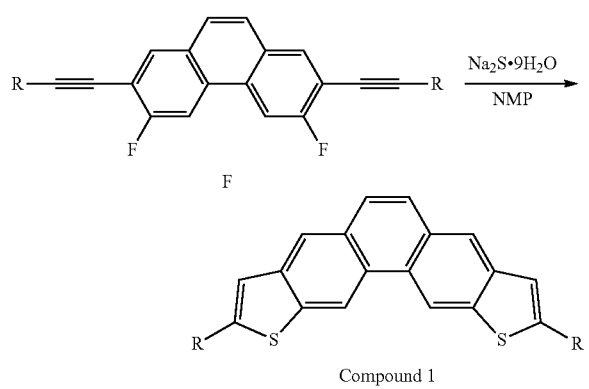

Compound 1

The compound 1 in which every R in the compound g shown in the above scheme 1 represents a n-octyl group was synthesized.

The compound 1 can be synthesized with reference to a known document (J. Am. Chem. Soc., 2011, 133, 5024).

The structure of the compound 1 was identified by $^1$H-NMR.

Compounds 2, 3, 5, 11, 13, 15, 16, and 24 represented by Formula (1) were synthesized in the same manner as in Synthesis of compound 1.

Each of the obtained compounds represented by Formula (1) was identified by elementary analysis, NMR, and MASS spectrometry.

<Synthesis of Comparative Compounds>

Comparative compounds 1 and 2 used in the semiconductor active layer (organic semiconductor layer) of comparative elements were synthesized according to the methods described in JP2011-46687A and KR-10-2012-0081539A. The comparative compound 1 is the compound 1 of JP2011-46687A, and the comparative compound 2 is the compound No. 133 of KR-10-2012-0081539A.

The structures of the comparative compounds 1 and 2 are shown below.

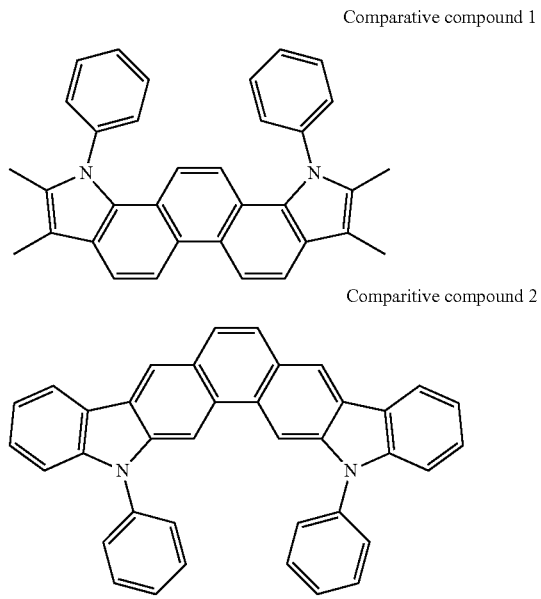

Comparative compound 1

Comparitive compound 2

Example 2

<Preparation/Evaluation of Element>

All of the materials used for preparing elements were purified by sublimation. Through high-performance liquid chromatography (TOSOH CORPORATION TSKgel ODS-100Z), it was confirmed that the materials had purity (area ratio for absorption intensity at 254 nm) of equal to or higher than 99.5%.

<Formation of Semiconductor Active Layer (Organic Semiconductor Layer) by Using Compound Alone>

Each of the compounds of the present invention or the comparative compounds (1 mg each) was mixed with toluene (1 mL) and heated to 100° C., thereby obtaining a coating solution for a non-light-emitting organic semiconductor device. In a nitrogen atmosphere, the coating solution was cast onto a substrate for measuring FET characteristics that was heated to 90° C., thereby forming an organic semiconductor film for a non-light-emitting organic semiconductor device. In this way, an organic transistor element of Example 2 for measuring FET characteristics was obtained. As the substrate for measuring FET characteristics, a silicon substrate comprising a bottom gate/bottom contact structure was used which included chromium/gold (gate width W=100 mm, gate length L=100 μm) arranged to form a comb pattern as source and drain electrodes and included SiO$_2$ (film thickness: 200 nm) as an insulating layer (the structure is schematically shown in FIG. 2).

[Evaluation]

By using a semiconductor parameter analyzer (4156C manufactured by Agilent Technologies) connected to a semi-automatic prober (AX-2000 manufactured by Vector Semiconductor Co., Ltd.), the FET characteristics of the organic transistor element of Example 2 were evaluated under a normal pressure/nitrogen atmosphere, from the viewpoint of the carrier mobility and the threshold voltage shift after repeated driving.

The obtained results are shown in the following Table 1.

(a) Carrier Mobility

Between the source electrode and the drain electrode of each organic film transistor element (FET element), a voltage of −80 V was applied, and the gate voltage was varied within a range of 20 V to −100 V. In this way, a carrier mobility t was calculated using the following equation showing a drain current $I_d$.

$$I_d = (W/2L)\mu C_i (V_g - V_{th})^2$$

In the equation, L represents a gate length, W represents a gate width, $C_i$ represents a capacity of the insulator layer per unit area, $V_g$ represents a gate voltage, and $V_{th}$ represents a threshold voltage.

Herein, because the characteristics of the element having a carrier mobility of less than $1 \times 10^{-5}$ cm$^2$/Vs were too poor, the element was not subjected to the evaluation of (b) threshold voltage shift after repeated driving described below.

(b) Threshold Voltage Shift after Repeated Driving

Between the source electrode and the drain electrode of each organic transistor element (FET element), a voltage of −80 V was applied, and the element was repeatedly driven 100 times by varying the gate voltage within a range of +20 V to −100 V. In this way, the element was measured in the same manner as in the section (a), and a difference between a threshold voltage $V_{before}$ before the repeated driving and a threshold voltage $V_{after}$ after the repeated driving (| $V_{after} - V_{before}$ |) was evaluated into 3 levels as below. The smaller the difference, the higher the stability of the element against repeated driving. Therefore, the smaller the difference, the more preferable.

| $V_{after} - V_{before}$ |≤5 V          A:

5 V<| $V_{after} - V_{before}$ |≤10 V      B:

| $V_{after} - V_{before}$ |>10 V         C:

(c) Solubility

Each of the compounds of the present invention or the comparative examples (20 mg each) was mixed with toluene (1 mL), and the solubility was evaluated into 2 levels as shown below.

A: Completely dissolved.
B: Incompletely dissolved.

TABLE 1

| Element No. | Organic semiconductor material | Carrier mobility (cm$^2$/Vs) | Threshold voltage shift after repeated driving | Solubility | Note |
|---|---|---|---|---|---|
| Element 1 | Compound 1 | $8.0 \times 10^{-3}$ | A | A | Present invention |
| Element 2 | Compound 2 | $2.2 \times 10^{-3}$ | A | A | Present invention |
| Element 3 | Compound 3 | $1.0 \times 10^{-3}$ | A | A | Present invention |
| Element 4 | Compound 5 | $2.6 \times 10^{-2}$ | A | A | Present invention |
| Element 5 | Compound 11 | $1.6 \times 10^{-2}$ | A | A | Present invention |
| Element 6 | Compound 13 | $1.3 \times 10^{-2}$ | A | A | Present invention |
| Element 7 | Compound 15 | $7.8 \times 10^{-3}$ | A | A | Present invention |
| Element 8 | Compound 16 | $9.4 \times 10^{-2}$ | A | A | Present invention |
| Element 9 | Compound 24 | $6.6 \times 10^{-2}$ | A | A | Present invention |
| Comparative element 1 | Comparative compound 1 | $5.8 \times 10^{-5}$ | C | B | Comparative example |
| Comparative element 2 | Comparative compound 2 | $3.3 \times 10^{-5}$ | C | B | Comparative example |

From the above Table 1, it was understood that the compound of the present invention exhibits excellent solubility in an organic solvent, and the organic transistor element using the compound of the present invention has high carrier mobility. Therefore, it was understood that the compound of the present invention can be preferably used as an organic semiconductor material for a non-light-emitting organic semiconductor device.

In contrast, the organic transistor element using the comparative compound 1 or 2 had low carrier mobility.

Herein, the organic transistor element using the compound of the present invention showed only a slight threshold voltage shift after repeated driving. Furthermore, the compound of the present invention exhibits excellent solubility in an organic solvent.

Example 3

<Formation of Semiconductor Active Layer (Organic Semiconductor Layer) by Using Compound and Binder Together>

Each of the compounds of the present invention or the comparative compounds (1 mg each) was mixed with 1 mg of PαMS (poly(α-methylstyrene), Mw=300,000), manufactured by Sigma-Aldrich Co, LLC.) and toluene (1 mL), and the mixture was heated to 100° C., thereby obtaining a coating solution. Organic transistor elements for measuring FET characteristics were prepared and evaluated in the same manner as in Example 2, except that the coating solution obtained as above was used.

The obtained results are shown in the following Table 2.

TABLE 2

| Element No. | Organic semiconductor material | Carrier mobility (cm$^2$/Vs) | Threshold voltage shift after repeated driving | Note |
|---|---|---|---|---|
| Element 10 | Compound 1 | $4.3 \times 10^{-2}$ | A | Present invention |
| Element 11 | Compound 5 | $7.3 \times 10^{-3}$ | A | Present invention |
| Element 12 | Compound 11 | $1.5 \times 10^{-2}$ | A | Present invention |
| Element 13 | Compound 16 | $1.2 \times 10^{-2}$ | A | Present invention |
| Comparative element 3 | Comparative compound 1 | $4.0 \times 10^{-5}$ | C | Comparative example |

TABLE 2-continued

| Element No. | Organic semiconductor material | Carrier mobility (cm²/Vs) | Threshold voltage shift after repeated driving | Note |
|---|---|---|---|---|
| Comparative element 4 | Comparative compound 2 | $5.8 \times 10^{-5}$ | C | Comparative example |

From the above Table 2, it was understood that the organic transistor element including a semiconductor active layer formed using the compound of the present invention with a binder has high carrier mobility. Therefore, it was understood that the compound of the present invention can be preferably used as an organic semiconductor material for a non-light-emitting organic semiconductor device.

In contrast, the organic transistor element including a semiconductor active layer formed using the comparative compound 1 or 2 with a binder had low carrier mobility.

Herein, the organic transistor element using the compound of the present invention showed only a slight threshold voltage shift after repeated driving.

Each of the organic transistor elements obtained in Example 3 was observed by unaided eyes and an optical microscope. As a result, it was understood that all of the films using PαMS as a binder have extremely high smoothness and uniformity.

From the above results, it was understood that in a case where the semiconductor active layer for the comparative element is formed using a binder and a comparative compound in combination, the carrier mobility becomes extremely low; however, in a case where the semiconductor active layer for the organic transistor element of the present invention is formed using the compound of the present invention with a binder, excellent carrier mobility is exhibited, and preferably, it is possible to obtain an element which shows only a slight threshold voltage shift after repeated driving and has extremely high smoothness/uniformity of the film

Example 4

<Formation of Semiconductor Active Layer (Organic Semiconductor Layer)>

The surface of a silicon wafer, which comprised $SiO_2$ (film thickness: 370 nm) as a gate insulating film, was treated with octyltrichlorosilane.

Each of the compounds of the present invention or the comparative compounds (1 mg each) was mixed with toluene (1 mL), and the mixture was heated to 100° C., thereby preparing a coating solution for a non-light-emitting organic semiconductor device. In a nitrogen atmosphere, the coating solution was cast onto the silicon wafer which had been heated to 90° C. and undergone surface treatment with octylsilane, thereby forming an organic semiconductor film for a non-light-emitting organic semiconductor device.

Furthermore, gold was deposited onto the surface of the film by using a mask so as to prepare source and drain electrodes, thereby obtaining an organic transistor element having a bottom gate/top contact structure with a gate width W=5 mm and a gate length L=80 μm (the structure is schematically shown in FIG. 1).

By using a semiconductor parameter analyzer (4156C manufactured by Agilent Technologies) connected to a semi-automatic prober (AX-2000 manufactured by Vector Semiconductor Co., Ltd.), the FET characteristics of the organic transistor element of Example 4 were evaluated in the same manner as in Example 2 under a normal pressure/nitrogen atmosphere.

The obtained results are shown in the following Table 3.

TABLE 3

| Element No. | Organic semiconductor material | Carrier mobility (cm²/Vs) | Threshold voltage shift after repeated driving | Note |
|---|---|---|---|---|
| Element 14 | Compound 1 | $1.5 \times 10^{-2}$ | A | Present invention |
| Element 15 | Compound 5 | $8.9 \times 10^{-3}$ | A | Present invention |
| Element 16 | Compound 11 | $6.5 \times 10^{-3}$ | A | Present invention |
| Element 17 | Compound 15 | $7.9 \times 10^{-3}$ | A | Present invention |
| Comparative element 5 | Comparative compound 1 | $4.8 \times 10^{-5}$ | C | Comparative example |
| Comparative element 6 | Comparative compound 2 | $6.4 \times 10^{-5}$ | C | Comparative example |

From the above Table 3, it was understood that the organic transistor element using the compound of the present invention has high carrier mobility. Therefore, it was understood that the compound of the present invention can be preferably used as an organic semiconductor material for a non-light-emitting organic semiconductor device.

In contrast, the organic transistor element using the comparative compound 1 or 2 had low carrier mobility.

Herein, the organic transistor element using the compound of the present invention showed only a slight threshold voltage shift after repeated driving.

EXPLANATION OF REFERENCES

11: substrate
12: electrode
13: insulator layer
14: semiconductor active layer (organic substance layer, organic semiconductor layer)
15a, 15b: electrode
31: substrate
32: electrode
33: insulator layer
34a, 34b: electrode
35: semiconductor active layer (organic substance layer, organic semiconductor layer)

What is claimed is:

1. An organic transistor comprising a compound represented by the following Formula (1) in a semiconductor active layer:

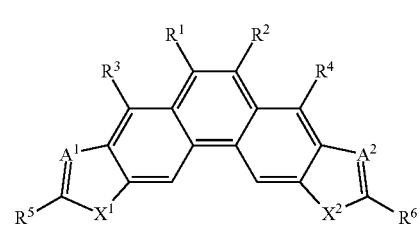

Formula (1)

in Formula (1),
each of $X^1$ and $X^2$ independently represents $NR^{13}$, an O atom, or a S atom, A¹ represents $CR^7$ or a N atom, A² represents $CR^8$ or a N atom, $R^{13}$ represents a hydrogen atom, an alkyl group, an alkenyl group, an alkynyl group, an acyl group, an aryl group, or a heteroaryl group, each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

-L-R      Formula (W)

in Formula (W), L represents a divalent linking group represented by any of the following Formulae (L-1) to (L-25) or a divalent linking group in which two or more divalent linking groups represented by one of the following Formulae (L-1) to (L-25) are bonded to each other, and R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

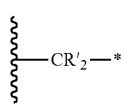
(L-1)

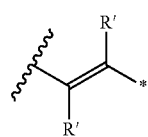
(L-2)

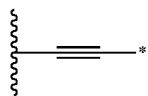
(L-3)

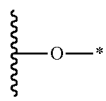
(L-4)

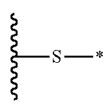
(L-5)

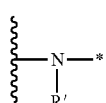
(L-6)

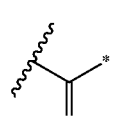
(L-7)

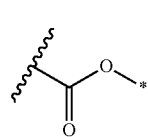
(L-8)

-continued

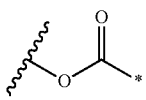
(L-9)

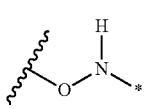
(L-10)

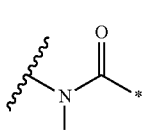
(L-11)

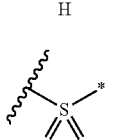
(L-12)

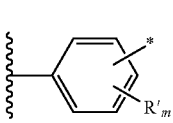
(L-13)

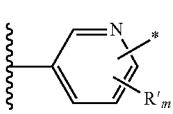
(L-14)

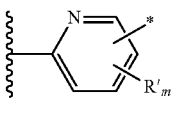
(L-15)

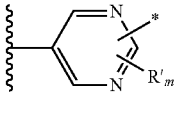
(L-16)

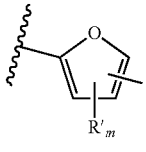
(L-17)

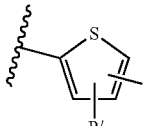
(L-18)

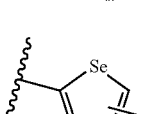
(L-19)

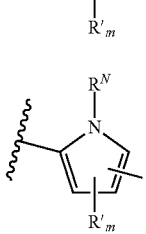
(L-20)

-continued

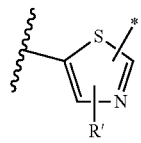 (L-21)

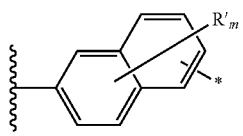 (L-22)

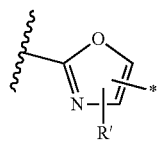 (L-23)

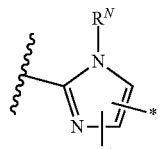 (L-24)

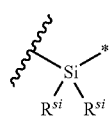 (L-25)

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

2. The organic transistor according to claim 1, wherein the compound represented by the Formula (1) is a compound represented by the following Formula (2-1) or (2-2);

Formula (2-1)

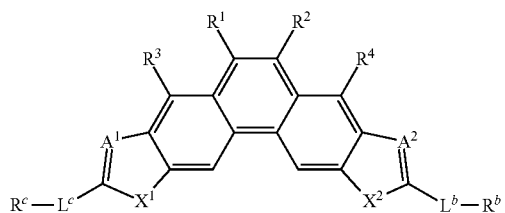

in Formula (2-1), each of $X^1$ and $X^2$ independently represents an O atom or a S atom, $A^1$ represents $CR^7$ or a N atom, $A^2$ represents $CR^8$ or a N atom, each of $R^1$ to $R^5$, $R^7$, and $R^8$ independently represents a hydrogen atom or a substituent, $R^5$ is not a group represented by -$L^a$-$R^a$, $L^a$ represents a divalent linking group represented by any of the following Formulae (L-1) to (L-25) or a divalent linking group in which two or more divalent linking groups represented by any of the following Formulae (L-1) to (L-25) are bonded to each other, and $R^a$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, an oligosiloxane group having two or more silicon atoms, a siloxane group, or a substituted or unsubstituted trialkylsilyl group;

Formula (2-2)

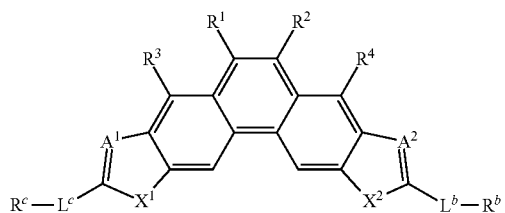

in Formula (2-2), each of $X^1$ and $X^2$ independently represents an O atom or a S atom, $A^1$ represents $CR^7$ or a N atom, $A^2$ represents $CR^8$ or a N atom, each of $R^1$ to $R^4$, $R^7$, and $R^8$ independently represents a hydrogen atom or a substituent, each of $L^b$ and $L^c$ independently represents a divalent linking group represented by any of the following Formulae (L-1) to (L-25) or a divalent linking group in which two or more divalent linking groups represented by any of the following Formulae (L-1) to (L-25) are bonded to each other, and each of $R^b$ and $R^c$ independently represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

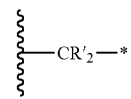 (L-1)

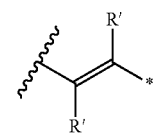 (L-2)

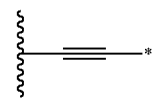 (L-3)

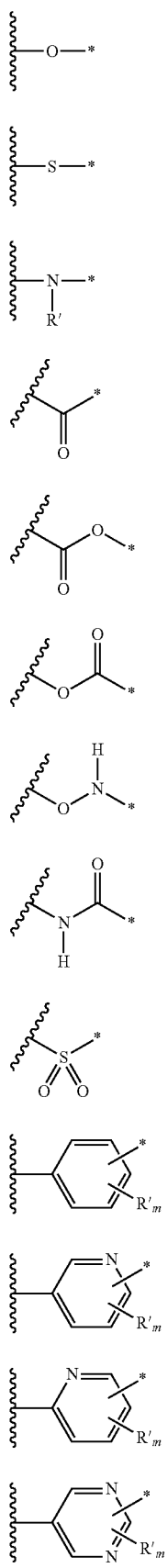
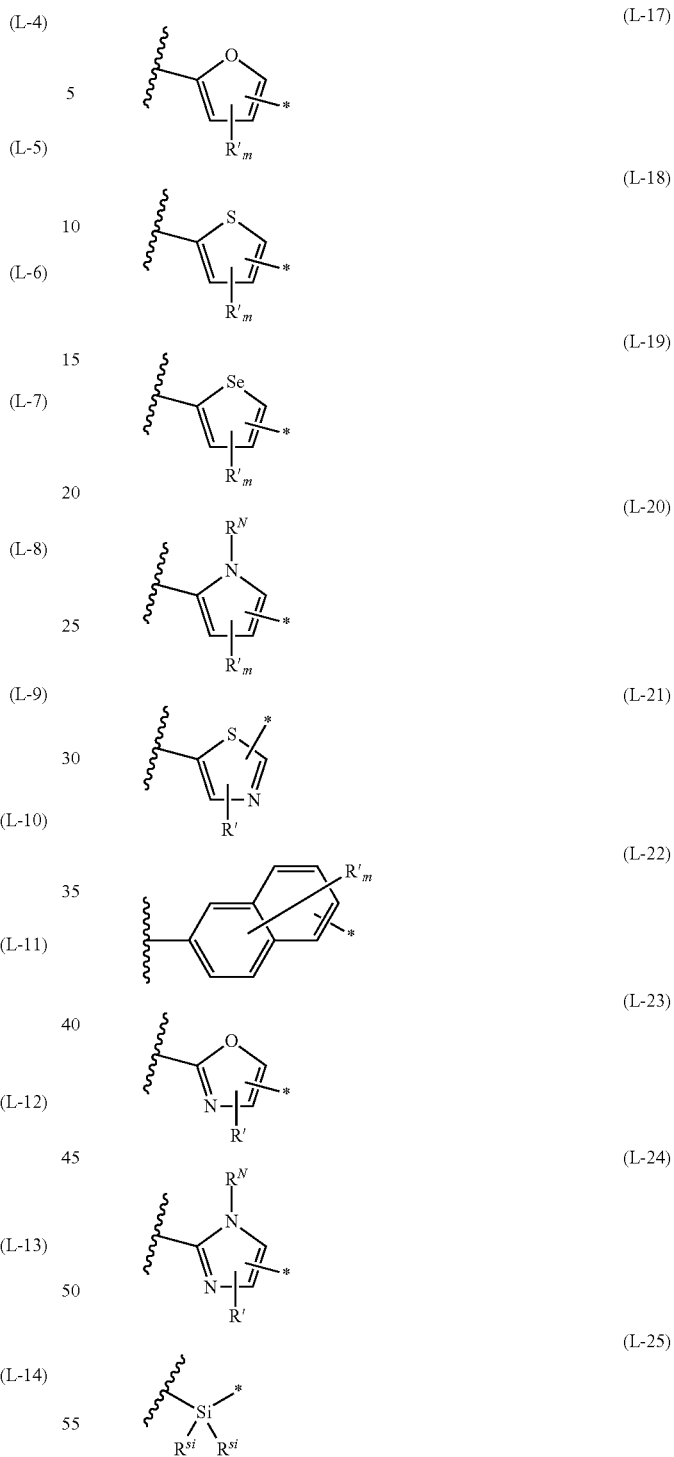
in Formulae (L-1) to (L-25), the portion of a wavy line represents a position of bonding to a phenanthrene skeleton condensed with two 5-membered heterocyclic rings,
m in Formula (L-13) represents 4, m in Formulae (L-14) and (L-15) represents 3, m in Formulae (L-16) to (L-20) represents 2, m in Formula (L-22) represents 6,
each R' in Formulae (L-1), (L-2), (L-6), and (L-13) to (L-24) independently represents a hydrogen atom or a substituent, $R^N$ represents a hydrogen atom or a substituent, and
each $R^{si}$ independently represents a hydrogen atom, an alkyl group, an alkenyl group, or an alkynyl group.

3. The organic transistor according to claim 1, wherein in the Formula (1), $A^1$ is $CR^7$ or $A^2$ is $CR^8$, and each of $R^7$ and $R^8$ independently represents a hydrogen atom or a substituent.

4. The organic transistor according to claim 1, wherein in the Formula (1), at least one of $X^1$ or $X^2$ is a S atom.

5. The organic transistor according to claim 1, wherein in the Formula (1), L is a divalent linking group represented by any of the Formulae (L-1) to (L-5), (L-13), (L-17), and (L-18) or a divalent linking group in which two or more divalent linking groups represented by any of the above formulae are bonded to each other.

6. The organic transistor according to claim 1, wherein in the Formula (1), L is a divalent linking group represented by any of the Formulae (L-1), (L-3), (L-13), and (L-18) or a divalent linking group in which a divalent linking group represented by any one of the Formulae (L-3), (L-13), and (L-18) is bonded to a divalent linking group represented by the Formula (L-1).

7. The organic transistor according to claim 1, wherein in the Formula (1), R is a substituted or unsubstituted alkyl group.

8. A compound represented by the following Formula (1):

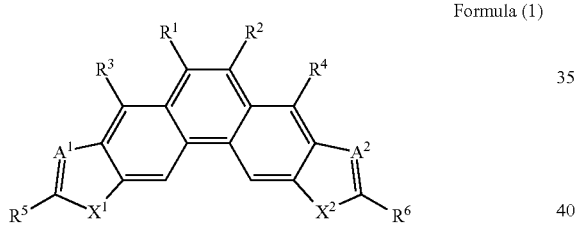

Formula (1)

in Formula (1),
each of $X^1$ and $X^2$ independently represents $NR^{13}$, an O atom, or a S atom,
$A^1$ represents $CR^7$ or a N atom, $A^2$ represents $CR^8$ or a N atom,
$R^{13}$ represents a hydrogen atom, an alkyl group, an alkenyl group, an alkynyl group, an acyl group, an aryl group, or a heteroaryl group,
each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

-L-R  Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, and
R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

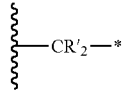 (L-1)

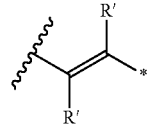 (L-2)

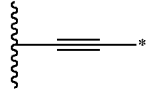 (L-3)

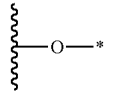 (L-4)

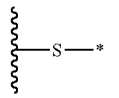 (L-5)

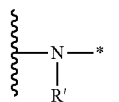 (L-6)

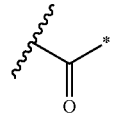 (L-7)

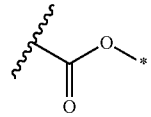 (L-8)

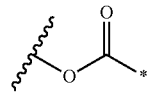 (L-9)

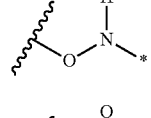 (L-10)

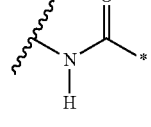 (L-11)

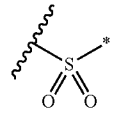 (L-12)

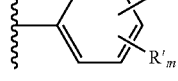 (L-13)

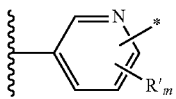 (L-14)

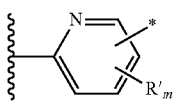 (L-15)

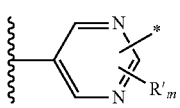 (L-16)

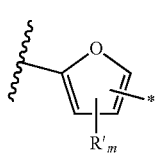 (L-17)

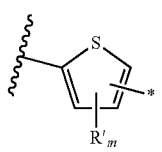 (L-18)

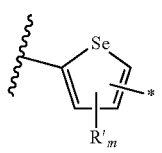 (L-19)

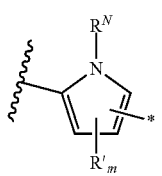 (L-20)

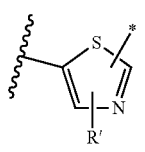 (L-21)

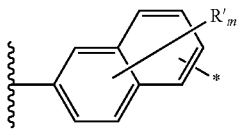 (L-22)

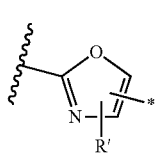 (L-23)

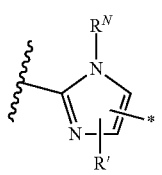 (L-24)

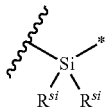 (L-25)

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

9. The compound according to claim 8, wherein the compound represented by the Formula (1) is a compound represented by the following Formula (2-1) or (2-2);

Formula (2-1)

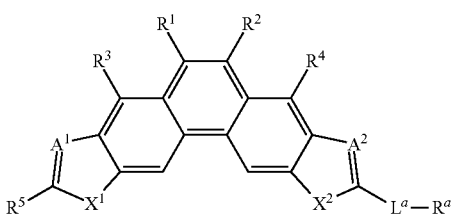

in Formula (2-1), each of $X^1$ and $X^2$ independently represents an O atom or a S atom, $A^1$ represents $CR^7$ or a N atom, $A^2$ represents $CR^8$ or a N atom, each of $R^1$ to $R^5$, $R^7$, and $R^8$ independently represents a hydrogen atom or a substituent, $R^5$ is not a group represented by -$L^a$-$R^a$, $L^a$ represents a divalent linking group represented by any of the following Formulae (L-1) to (L-25) or a divalent linking group in which two or more divalent linking groups represented by any of the following Formulae (L-1) to (L-25) are bonded to each other, and $R^a$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, an oligosiloxane group having two or more silicon atoms, a siloxane group, or a substituted or unsubstituted trialkylsilyl group;

Formula (2-2)

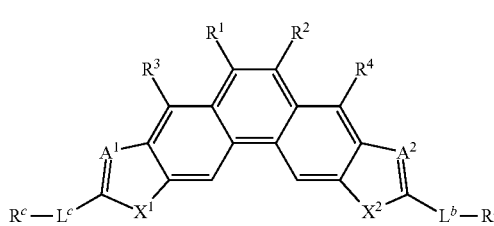

in Formula (2-2), each of $X^1$ and $X^2$ independently represents an O atom or a S atom, $A^1$ represents $CR^7$ or a N atom, $A^2$ represents $CR^8$ or a N atom, each of $R^1$ to $R^4$, $R^7$, and $R^8$ independently represents a hydrogen atom or a substituent, each of $L^b$ and $L^c$ independently represents a divalent linking group represented by any of the following Formulae (L-1) to (L-25) or a divalent linking group in which two or more divalent linking groups represented by any of the following Formulae (L-1) to (L-25) are bonded to each other, and each of $R^b$ and $R^c$ independently represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

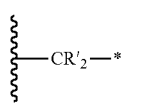  (L-1)

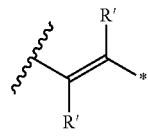  (L-2)

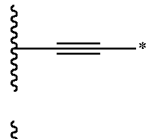  (L-3)

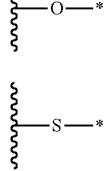  (L-4)

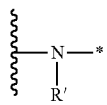  (L-5)

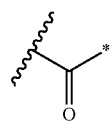  (L-6)

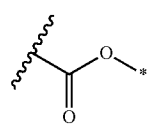  (L-7)

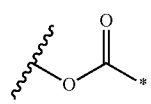  (L-8)

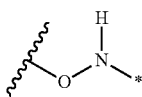  (L-9)

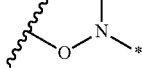  (L-10)

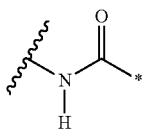  (L-11)

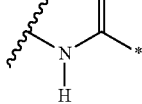  (L-12)

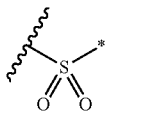  (L-13)

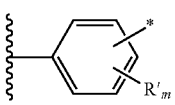  (L-14)

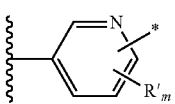  (L-15)

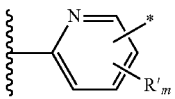  (L-16)

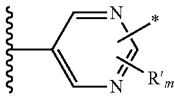  (L-17)

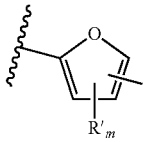  (L-18)

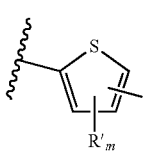  (L-19)

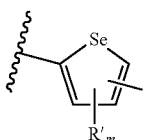  (L-20)

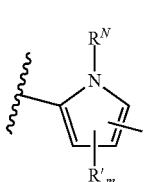  (L-21)

-continued

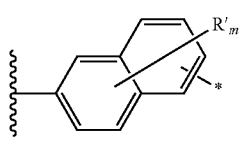
(L-22)

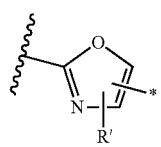
(L-23)

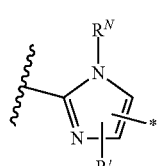
(L-24)

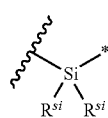
(L-25)

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

10. The compound according to claim 8, wherein in the Formula (1), $A^1$ is $CR^7$ or $A^2$ is $CR^8$, and each of $R^7$ and $R^8$ independently represents a hydrogen atom or a substituent.

11. The compound according to claim 8, wherein in the Formula (1), at least one of $X^1$ or $X^2$ is a S atom.

12. The compound according to claim 8, wherein in the Formula (1), L is a divalent linking group represented by any of the Formulae (L-1) to (L-5), (L-13), (L-17), and (L-18) or a divalent linking group in which two or more divalent linking groups represented by any of the above formulae are bonded to each other.

13. The compound according to claim 8, wherein in the Formula (1), L is a divalent linking group represented by any of the Formulae (L-1), (L-3), (L-13), and (L-18) or a divalent linking group in which a divalent linking group represented by any one of the Formulae (L-3), (L-13), and (L-18) is bonded to a divalent linking group represented by the Formula (L-1).

14. The compound according to claim 8, wherein in the Formula (1), R is a substituted or unsubstituted alkyl group.

15. An organic semiconductor material for a non-light-emitting organic semiconductor device, comprising the compound according to claim 8.

16. A material for an organic transistor, comprising the compound according to claim 8.

17. A coating solution for a non-light-emitting organic semiconductor device, comprising the compound according to claim 8.

18. The coating solution for a non-light-emitting organic semiconductor device according to claim 17, further comprising a polymer binder.

19. An organic semiconductor film for a non-light-emitting organic semiconductor device, comprising the compound according to claim 8.

20. The organic semiconductor film for a non-light-emitting organic semiconductor device according to claim 19, further comprising a polymer binder.

21. The organic semiconductor film for a non-light-emitting organic semiconductor device according to claim 19 that is prepared by a solution coating method.

22. A compound represented by the following Formula (3);

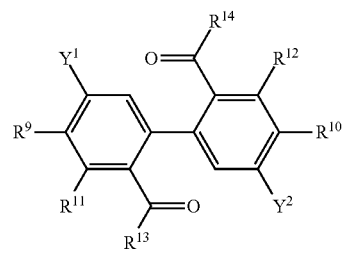

Formula (3)

in Formula (3), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, and each of $R^{11}$ to $R^{14}$ independently represents a hydrogen atom or a substituent.

23. A compound represented by the following Formula (4);

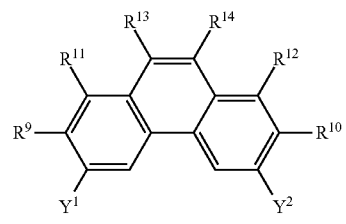

Formula (4)

in Formula (4), each of $Y^1$ and $Y^2$ independently represents a halogen atom, each of $R^9$ and $R^{10}$ independently represents a halogen atom, a carbonyl group, a trialkylsilyl group, an alkynyl group, or an alkenyl group, each of $R^{11}$ to $R^{14}$ independently represents a hydrogen atom or a substituent, and at least one of $R^{13}$ and $R^{14}$ represents a hydrogen atom.

24. The compound according to claim 22 that is an intermediate compound of a compound represented by the following Formula (1):

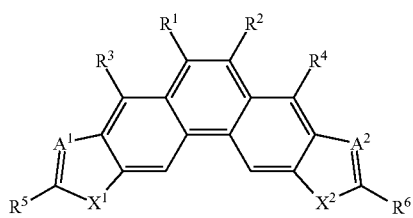

Formula (1)

in Formula (1),
each of $X^1$ and $X^2$ independently represents $NR^{13}$, an O atom, or a S atom,
$A^1$ represents $CR^7$ or a N atom, $A^2$ represents $CR^8$ or a N atom,
$R^{13}$ represents a hydrogen atom, an alkyl group, an alkenyl group, an alkynyl group, an acyl group, an aryl group, or a heteroaryl group,
each of $R^1$ to $R^8$ independently represents a hydrogen atom or a substituent, and at least one of $R^1$, $R^2$, $R^3$, $R^4$, $R^5$, $R^6$, $R^7$, or $R^8$ is a substituent represented by the following Formula (W):

-L-R  Formula (W)

in Formula (W), L represents a divalent linking group represented by any of the following Formulae (L-1) to (L-25) or a divalent linking group in which two or more divalent linking groups represented by any of the following Formulae (L-1) to (L-25) are bonded to each other, and R represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group;

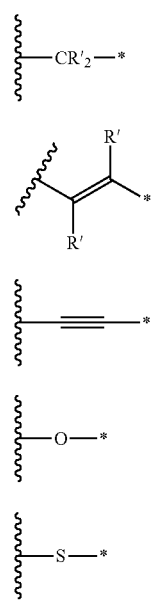

-continued

(L-6)

(L-7)

(L-8)

(L-9)

(L-10)

(L-11)

(L-12)

(L-13)

(L-14)

(L-15)

(L-16)

(L-17)

(L-18)

-continued (L-19) 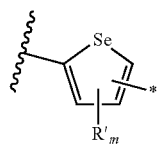

(L-20) 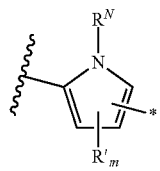

(L-21) 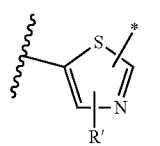

(L-22) 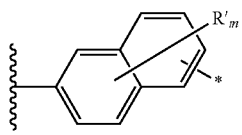

(L-23) 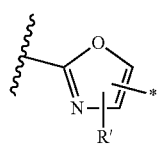

(L-24) 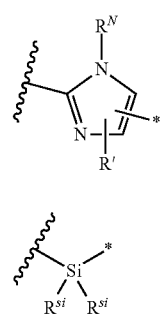

(L-25) 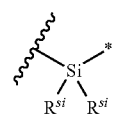

in Formulae (L-1) to (L-25), the portion of a wavy line represents a position of bonding to a phenanthrene skeleton condensed with two 5-membered heterocyclic rings, m in Formula (L-13) represents 4, m in Formulae (L-14) and (L-15) represents 3, m in Formulae (L-16) to (L-20) represents 2, m in Formula (L-22) represents 6, each R' in Formulae (L-1), (L-2), (L-6), and (L-13) to (L-24) independently represents a hydrogen atom or a substituent, $R^N$ represents a hydrogen atom or a substituent, and each $R^{si}$ independently represents a hydrogen atom, an alkyl group, an alkenyl group, or an alkynyl group.

* * * * *